US011149068B2

(12) United States Patent
Wimley et al.

(10) Patent No.: US 11,149,068 B2
(45) Date of Patent: Oct. 19, 2021

(54) PORE-FORMING PEPTIDES AND USES THEREOF

(71) Applicants: The Administrators of the Tulane Educational Fund, New Orleans, LA (US); The Johns Hopkins University, Baltimore, MD (US)

(72) Inventors: William C. Wimley, New Orleans, LA (US); Gregory Wiedman, New Orleans, LA (US); Kalina Hristova, New Orleans, LA (US); Sarah Y. Kim, New Orleans, LA (US)

(73) Assignees: The Administrator of the Tulane Educational Fund, New Orleans, LA (US); The John Hopkins University, Baltimore, MD (US)

( * ) Notice: Subject to any disclaimer, the term of this patent is extended or adjusted under 35 U.S.C. 154(b) by 135 days.

(21) Appl. No.: 16/231,738

(22) Filed: Dec. 24, 2018

(65) Prior Publication Data

US 2019/0211063 A1    Jul. 11, 2019

Related U.S. Application Data

(60) Provisional application No. 62/614,090, filed on Jan. 5, 2018.

(51) Int. Cl.
| | | |
|---|---|---|
| *A61K 38/04* | (2006.01) | |
| *C07K 14/00* | (2006.01) | |
| *A61K 49/00* | (2006.01) | |
| *A61P 35/00* | (2006.01) | |
| *A61K 9/127* | (2006.01) | |

(52) U.S. Cl.
CPC .......... *C07K 14/001* (2013.01); *A61K 9/1271* (2013.01); *A61K 49/0002* (2013.01); *A61P 35/00* (2018.01)

(58) Field of Classification Search
None
See application file for complete search history.

(56) References Cited

U.S. PATENT DOCUMENTS

| 2014/0024597 A1 | 1/2014 | Troy et al. |
| 2019/0211063 A1 | 7/2019 | Wimley et al. |

FOREIGN PATENT DOCUMENTS

| CA | 2991223 A1 | 7/2019 |
| WO | WO-2016/142445 A2 | 9/2016 |

OTHER PUBLICATIONS

Wiedman, J. Am. Chem. Soc. Jan. 18, 2017; 139(2): 937-945 (cited in IDS dated Apr. 23, 2019) (Year: 2017).*

Krauson et al., "Conformational Fine-Tuning of Pore-Forming Peptide Potency and Selectivity," J Am Chem Soc. 137(51): 16144-52 (2015).
Wiedman et al., "Highly Efficient Macromolecule-Sized Poration of Lipid Bilayers by a Synthetically Evolved Peptide," J Am Chem Soc. 136(12): 4724-31 (2014).
Wiedman et al., "Testing the limits of rational design by engineering pH sensitivity into membrane active peptides," available in PMC Apr. 1, 2016, published in final edited form as: Biochim Biophys Acta. 1848(4):951-7 (2015) (15 pages).
Farrand et al., "The Cholesterol-dependent Cytolysin Membrane-binding Interface Discriminates Lipid Environments of Cholesterol to Support β-Barrel Pore Insertion," J Biol Chem. 290(29): 17733-44 (2015).
Wiedman et al., "PH-Triggered, Macromolecule-Sized Poration of Lipid Bilayers by Synthetically Evolved Peptides," available in PMC Jul. 21, 2017, published in final edited form as: J Am Chem Soc. 139(2):937-45 (2017) (22 pages).
International Search Report and Written Opinion for International Application No. PCT/US18/57614, dated Feb. 25, 2019 (17 pages).
International Preliminary Report on Patentability for International Application No. PCT/US18/57614, dated Apr. 28, 2020 (7 pages).
Hristova et al., "A look at arginine in membranes," available in PMC Jan. 1, 2012, published in final edited form as: J Membr Biol. 239(1-2):49-56 (2011) (13 pages).
Starr et al., "Pituitary adenylate cyclase-activating polypeptide is a potent broad-spectrum antimicrobial peptide: Structure-activity relationships," available in PMC Jun. 1, 2019, published in final edited form as: Peptides. 104:35-40 (2018) (19 pages).
Starr et al., "Antimicrobial peptides are degraded by the cytosolic proteases of human erythrocytes," available in PMC Dec. 1, 2018, published in final edited form as: Biochim Biophys Acta. 1859(12):2319-26 (2017) (20 pages).
Wimley, "Application of Synthetic Molecular Evolution to the Discovery of Antimicrobial Peptides," available in PMC Oct. 8, 2019, published in final edited form as: Adv Exp Med Biol. 1117: 241-255 (2019) (20 pages).
Wimley et al., "Antimicrobial Peptides: successes, challenges and unanswered questions," available in PMC Sep. 2, 2011, published in final edited form as: J Membr Biol. 239(1-2):27-34 (2011) (12 pages).
Krauson et al., "Determining the mechanism of membrane permeabilizing peptides: Identification of potent, equilibrium pore-formers," available in PMC Jul. 1, 2013, published in final edited form as: Biochim Biophys Acta. 1818(7): 1625-32 (2012) (20 pages).
Rathinakumar et al., "Broad-spectrum Antimicrobial Peptides by Rational Combinatorial Design and High-throughput Screening: The Importance of Interfacial Activity," available in PMC Sep. 8, 2010, published in final edited form as: J Am Chem Soc. 131(22):7609-17 (2009) (23 pages).
He et al., "A Lack of Synergy Between Membrane-permeabilizing Cationic Antimicrobial Peptides and Conventional Antibiotics," available in PMC Jan. 1, 2016, published in final edited form as: Biochim Biophys Acta. 1848(100):8-15 (2015) (21 pages).

(Continued)

*Primary Examiner* — Satyanarayana R Gudibande
(74) *Attorney, Agent, or Firm* — Clark & Elbing LLP

(57) ABSTRACT

Described herein are membrane permeabilizing peptides, polynucelotides encoding the peptides, and lipid vesicles comprising the peptides. Furthermore, described herein are methods for using the peptides, polynucleotides, and lipid vesicles for research, diagnosis, disease prevention, and therapeutic treatment.

21 Claims, 7 Drawing Sheets

Specification includes a Sequence Listing.

(56) References Cited

OTHER PUBLICATIONS

Wimley, "Describing the Mechanism of Antimicrobial Peptide Action with the Interfacial Activity Model," available in PMC Oct. 15, 2011, published in final edited form as: ACS Chem Biol. 15(10):905-17 (2010) (21 pages).
Rausch et al., "Beta-Sheet Pore-Forming Peptides Selected from a Rational Combinatorial Library: Mechanism of Pore Formation in Lipid Vesicles and Activity in Biological Membranes," available in PMC Nov. 14, 2008, published in final edited form as: Biochemistry. 46(43):12124-39 (2007) (37 pages).
Starr et al., "Host Cell Interactions are a Significant Barrier to the Clinical Utility of Peptide Antibiotics," available in PMC Jul. 21, 2017, published in final edited form as: ACS Chem Biol. 11(12):3391-99 (2016) (18 pages).
Walkenhorst et al., "pH Dependence of Microbe Sterilization by Cationic Antimicrobial Peptides," Antimicrob Agents Chemother. 57(7) 2013:3312-20 (2013).
Chang et al., "Characterization of antimicrobial peptide activity by electrochemical impedance spectroscopy," available in PMC Oct. 1, 2009, published in final edited form as: Biochim Biophys Acta. 1778(10):2430-36 (2008) (16 pages).
Rathinakumar et al., "High-throughput discovery of broad-spectrum peptide antibiotics," FASEB J. 24(9):3232-38 (2010) (11 pages).
Ladokhin et al., "Leakage of Membrane Vesicle Contents: Determination of Mechanism Using Fluorescence Requenching," Biophys J. 69(5):1964-71 (1995).
Krauson et al., "Synthetic molecular evolution of pore-forming peptides by Iterative combinatorial library screening," available in PMC Apr. 19, 2014, published in final edited form as: ACS Chem Biol. 8(4):823-31 (2013) (18 pages).
Wimley et al., "Interactions between human defensins and lipid bilayers: evidence for formation of multimeric pores," Protein Sci. 3(9):1362-73 (1994).
Starr et al., "Synthetic molecular evolution of host cell-compatible, antimicrobial peptides effective against drug-resistant, biofilm-forming bacteria," Proc Natl Acad Sci U S A. 117(15):8437-48 (2020) (8 pages) (Abstract only).
Chen et al., "Simulation-Guided Rational de Novo Design of a Small Pore-Forming Antimicrobial Peptide," J Am Chem Soc. 141(12):4839-48 (2019) (1 page) (Abstract only).
White et al., "Structure, function, and membrane integration of defensins," Curr Opin Struct Biol. 5(4):521-7 (1995) (1 page) (Abstract only).
Wang et al., "Burkholderia thailandensis outer membrane vesicles exert antimicrobial activity against drug-resistant and competitor microbial species," J Microbiol. 58(7):550-62 (2020) (1 page) (Abstract only).
Lin et al., "Interactions of membrane active peptides with planar supported bilayers: an impedance spectroscopy study," Langmuir. 28(14):6088-96 (2012) (1 page) (Abstract only).
Lam et al., "Effective endogenous gene silencing mediated by pH responsive peptides proceeds via multiple pathways," J Control Release. Mar. 10, 2012;158(2):293-303. doi: 10.1016/j.jconrel.2011. 11.024. Epub Nov. 26, 2011. PMID: 22138072; PMCID: PMC3309421.
Kauffman et al., "Mechanism Maters: A Taxonomy of Cell Penetrating Peptides," Trends Biochem. Sci. 40 (12), 749-764 (2015).
Soman et al., "Molecularly targeted nanocarriers deliver the cytolytic peptide melittin specifically to tumor cells in mice, reducing tumor growth," Journal of Clinical Investigation. 119 (9):2830-2842 (2009).
Andreev et al., "pH-sensitive membrane peptides (pHLIPs) as a novel class of delivery agents," Mol Membr Biol. 27 (7): 341-352 (2010).
Heitz et al., "Twenty years of cell-penetrating peptides: from molecular mechanisms to therapeutics," Br J Pharmacol. 157 (2):195-206 (2009).
Bechinger, B. "Peptide-nucleic acid nanostructures for transfection," Biomol Concepts. 3 (3):283-293 (2012).
Raagel et al., "Peptide-mediated protein delivery—Which pathways are penetrable?" Biochim Biophys Acta. 1798 (12):2240-2248 (2010).
Hallbrink et al., "Cargo delivery kinetics of cell-penetrating peptides," Biochim Biophys Acta. 1515 (2):101-109 (2001).
Lam et al., "Effective endogenous gene silencing mediated by pH responsive peptides proceeds via multiple pathways," J Control Release. 158 (2):293-303 (2012).
Pantaleo et al., "Molecular imaging and targeted therapies in oncology: New concepts in treatment response assessment. A collection of cases," Int J Oncol. 33 (3):443-452 (2008).
Gillies et al., "Causes and consequences of increased glucose metabolism of cancers," J Nucl Med. 49 Suppl 2:24S-42S (2008).
Muro, "Challenges in design and characterization of ligand-targeted drug delivery systems," J Control Release. 164 (2):125-137 (2012).
Yu et al., "Overcoming Endosomal Barrier by Amphotericin B-Loaded Dual pH-Responsive PDMA-b-PDPA Micelleplexes for siRNA Delivery," Acs Nano. 5 (11):9246-9255 (2011).
Yao et al., "pHLIP (R)-mediated delivery of PEGylated liposomes to cancer cells," J Control Release. 167 (3):228-237 (2013).
Fendos et al., "Aspartate Embedding Depth Affects pHLIP's Insertion pK(a)," Biochemistry. 52 (27):4595-4604 (2013).
An et al., "pH-(low)-insertion-peptide (pHLIP) translocation of membrane impermeable phalloidin toxin inhibits cancer cell proliferation," Proc Natl Acad Sci U S A. 107 (47):20246-20250 (2010).
Nishimura et al., "A display of pH-sensitive fusogenic GALA peptide facilitates endosomal escape from a Bio-nanocapsule via an endocytic uptake pathway," J Nanobiotechnology. 12:11 (2014).
Wiedman et al., "The electrical response of bilayers to the bee venom toxin melittin: Evidence for transient bilayer permeabilization," Biochim Biophys Acta. 1828 (5):1357-1364 (2013).
Krauson et al., "Gain-of-Function Analogues of the Pore-Forming Peptide Melittin Selected by Orthogonal High-Throughput Screening," J Am Chem Soc. 134 (30):12732-12741 (2012).
Wimley et al., "Folding of beta-sheet membrane proteins: a hydrophobic hexapeptide model," J Mol Biol. 277(5):1091-1110 (1998).
Mayer et al., "Vesicles of variable sizes produced by a rapid extrusion procedure," Biochim Biophys Acta. 858(1):161-168 (1986).
Bechinger, B. "Structure and function of membrane-lytic peptides," Critical Reviews in Plant Sciences. 23 (3):271-292 (2004).
Snider et al., "MPEx: A tool for exploring membrane proteins," Protein Sci. 18 (12):2624-2628 (2009).
Erazo-Oliveras et al., "Improving the endosomal escape of cell-penetrating peptides and their cargos: strategies and challenges," Pharmaceuticals (Basel). 5 (11):1177-1209 (2012).
Wimley et al., "The Mechanism of Membrane Permeabilization by Peptides: Still an Enigma," Aust J Chem. 73(3):96-103 (2019).
Rausch et al., "Rational combinatorial design of pore-forming beta-sheet peptides," Proceedings of the National Academy of Sciences of the United States of America. 102(30):10511-10515 (2005). https://doi.org/10.1073/pnas.0502013102.
Rathinakumar et al., "Biomolecular engineering by combinatorial design and high-throughput screening: small, soluble peptides that permeabilize membranes," Journal of the American Chemical Society. 130(30):9849-9858 (2008). https://doi.org/10.1021/ja8017863.
Gerlach et al., "Anticancer and chemosensitizing abilities of cycloviolacin 02 from Viola odorata and psyle cyclotides from Psychotria leptothyrsa," Biopolymers. 94(5):617-25 (2010).
He et al., "Toward the de novo design of antimicrobial peptides: Lack of correlation between peptide permeabilization of lipid vesicles and antimicrobial, cytolytic, or cytotoxic activity in living cells," Biopolymers. 102(1):1-6 (2014).
Parente et al., "Mechanism of Leakage of Phospholipid Vesicle Contents Induced by the Peptide GALA," Biochemistry. 29(37) 8720-8728 (1990) (8 pages).
VanDyke, R. "Acidification of Lysosomes and Endosomes," Subcell Biochem. 27:331-360 (1996) (30 pages).
Wimley, W., "Energetics of peptides and Protein Binding to Lipid Membranes,"Adv Exp Med Biol. 677:14-23 (2010) (10 pages).
Lehrer et al., "Defensins: Endogenous Antibiotic Peptides of Animal Cells," Cell. 64(2):229-230 (1991) (2 pages).
Maiolo et al., "Specific Redistribution of Cell-Penetrating Peptides from Endosomes to the Cytoplasm and Nucleus upon Laser Illumination," JACS. 126(47):15376-15377 (2004) (2 pages).

(56) References Cited

OTHER PUBLICATIONS

Parente et al., "Association of a pH-Sensitive Peptide with Membrane Vesicles: Role of Amino Acid Sequence," *Biochemistry.* 29(37): 8713-8719 (1990) (7 pages).

Subbarao et al., "pH-Dependent Bilayer Destabilization by an Amphipathic Peptide," *Biochemistry.* 26(11):2964-2972 (1987) (9 pages).

Kakudo et al., "Transferrin-Modified Liposomes Equipped with a pH-Sensitive Fusogenic Peptide: An Artificial Viral-like Delivery System," *Biochemistry.* 43:5618-5628 (2004) (11 pages).

Kullberg et al., "Listeriolysin O enhances cytoplasmic delivery by Her-2 targeting liposomes," *J Drug Target.* 18(4):313-320 (2010) (8 pages).

Ganz et al., "Defensins," *Eur J Haematol.* 44(1):1-8 (1990).

Oliveira et al., "Fusogenic peptides enhance endosomal escape improving siRNA-induced silencing of oncogenes," *Inter J Pharamaceut.* 331 (2):211-214 (2007).

Shai et al., "From "carpet" mechanism to de-novo designed diastereomeric cell-selective antimicrobial peptides," *Peptides.* 22 (10):1629-1641 (2001).

Komin ert al., "Peptide-based strategies for enhanced cell uptake, transcellular transport, and circulation: Mechanisms and challenges," *Adv Drug Deliv Rev.* 110-111:52-64 (2017).

Duncan, R. "The dawning era of polymer therapeutics," *Nat Rev Drug Discov.* 2 (5):347-360 (2003).

Varkouhi et al., "Endosomal escape pathways for delivery of biologicals," *J Control Release.* 151 (3):220-228(2011).

Endoh et al., "Cellular siRNA delivery using cell-penetrating peptides modified for endosomal escape," *Adv Drug Deliv Rev.* 61 (9):704-709 (2009).

White et al., "Protein folding in membranes: Determining the energetics of peptide-bilayer interactions," *Methods Enzymol.* 295:62-87 (1998).

Brown et al., "Cationic host defense (antimicrobial) peptides," *Curr Opin Immunol.* 18(1): 24-30 (2006).

Dempsey, C. E. "The action of melittin on membranes," *Biochim Biophys Acta.* 1031(2):143-161 (1990).

Akinc et al., "Exploring polyethylenimine-mediated DNA transfection and the proton sponge hypothesis," *J Gene Med.* 7 (5):657-663 (2005).

Wimley et al., "Determining the membrane topology of peptides by fluorescence quenching," *Biochemistry.* 39(1):161-70 (2000).

Rausch et al., "A high-throughput screen for identifying transmembrane pore-forming peptides," *Anal Biochem.* 293(2):258-63 (2001).

\* cited by examiner

FIG. 1A
FIG. 1B
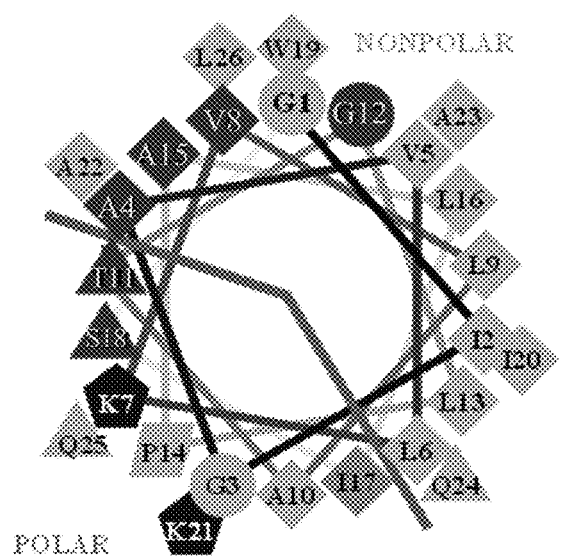
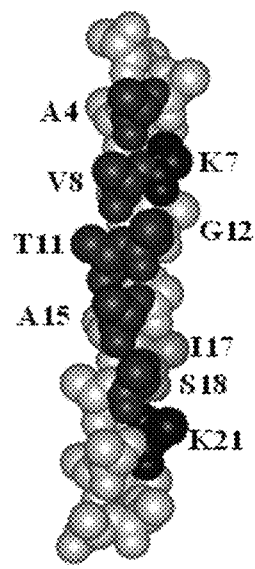
FIG. 1C GIGAVLKVLATGLPALISWIKAAQQL
Possible residues in each varied site
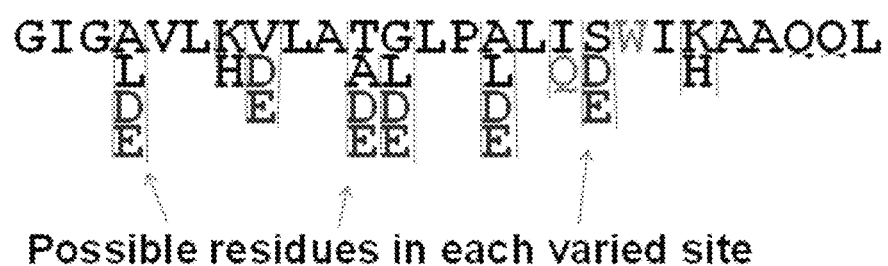

FIG. 2A   pH 7 ANTS/DPX Assay
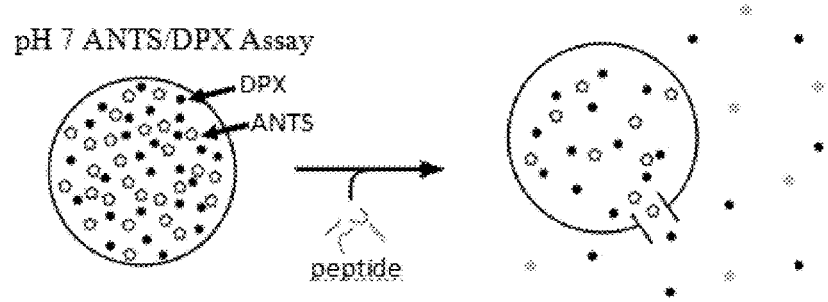
FIG. 2B   pH 5 FRET Assay
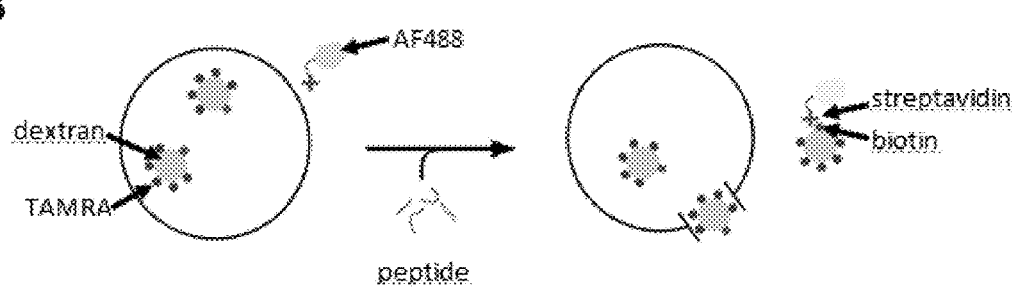

SEQUENCE LISTING

```
<160> NUMBER OF SEQ ID NOS: 18

<210> SEQ ID NO 1
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is an acidic amino acid
<220> FEATURE:
<221> NAME/KEY: MISC_FEATURE
<222> LOCATION: (7)..(7)
<223> OTHER INFORMATION: Xaa is a basic amino acid
<220> FEATURE:
<221> NAME/KEY: MISC_FEATURE
<222> LOCATION: (8)..(8)
<223> OTHER INFORMATION: Xaa is an acidic amino acid
<220> FEATURE:
<221> NAME/KEY: MISC_FEATURE
<222> LOCATION: (11)..(12)
<223> OTHER INFORMATION: Xaa is a nonpolar or acidic amino acid
<220> FEATURE:
<221> NAME/KEY: MISC_FEATURE
<222> LOCATION: (15)..(15)
<223> OTHER INFORMATION: Xaa is a nonpolar or acidic amino acid
<220> FEATURE:
<221> NAME/KEY: MISC_FEATURE
<222> LOCATION: (18)..(18)
<223> OTHER INFORMATION: Xaa is a polar or acidic amino acid
<220> FEATURE:
<221> NAME/KEY: MISC_FEATURE
<222> LOCATION: (21)..(21)
<223> OTHER INFORMATION: Xaa is a basic amino acid
```

<400> SEQUENCE: 1

Gly Ile Gly Xaa Val Leu Xaa Xaa Leu Ala Xaa Xaa Leu Pro Xaa Leu
1               5                   10                  15

Gln Xaa Trp Ile Xaa Ala Ala Gln Gln Leu
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asp or Glu
<220> FEATURE:
<221> NAME/KEY: MISC_FEATURE
<222> LOCATION: (7)..(7)
<223> OTHER INFORMATION: Xaa is His or Lys
<220> FEATURE:
<221> NAME/KEY: MISC_FEATURE
<222> LOCATION: (8)..(8)
<223> OTHER INFORMATION: Xaa is Asp or Glu
<220> FEATURE:
<221> NAME/KEY: MISC_FEATURE
<222> LOCATION: (11)..(11)
<223> OTHER INFORMATION: Xaa is Ala, Asp, or Glu
<220> FEATURE:
<221> NAME/KEY: MISC_FEATURE
<222> LOCATION: (12)..(12)
<223> OTHER INFORMATION: Xaa is Gly, Leu, Asp, or Glu
<220> FEATURE:
<221> NAME/KEY: MISC_FEATURE
<222> LOCATION: (15)..(15)
<223> OTHER INFORMATION: Xaa is Ala, Leu, Asp, or Glu
<220> FEATURE:
<221> NAME/KEY: MISC_FEATURE
<222> LOCATION: (18)..(18)
<223> OTHER INFORMATION: Xaa is Ser, Asp, or Glu
<220> FEATURE:
<221> NAME/KEY: MISC_FEATURE
<222> LOCATION: (21)..(21)
<223> OTHER INFORMATION: Xaa is His or Lys

<400> SEQUENCE: 2

Gly Ile Gly Xaa Val Leu Xaa Xaa Leu Ala Xaa Xaa Leu Pro Xaa Leu
1               5                   10                  15

Gln Xaa Trp Ile Xaa Ala Ala Gln Gln Leu
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic Construct

<400> SEQUENCE: 3

Gly Ile Gly Glu Val Leu His Glu Leu Ala Asp Asp Leu Pro Asp Leu
1               5                   10                  15

Gln Glu Trp Ile His Ala Ala Gln Gln Leu
            20                  25

<210> SEQ ID NO 4
<211> LENGTH: 26
<212> TYPE: PRT
<213> ORGANISM: Artificial Sequence
<220> FEATURE:

```
<223> OTHER INFORMATION: Synthetic Construct

<400> SEQUENCE: 4

Gly Ile Gly Asp Val Leu His Glu Leu Ala Ala Asp Leu Pro Glu Leu
1               5                   10                  15

Gln Glu Trp Ile His Ala Ala Gln Gln Leu
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Construct

<400> SEQUENCE: 5

Gly Ile Gly Glu Val Leu Lys Glu Leu Ala Ala Asp Leu Pro Glu Leu
1               5                   10                  15

Gln Asp Trp Ile Lys Ala Ala Gln Gln Leu
            20                  25

<210> SEQ ID NO 6
<211> LENGTH: 26
<212> TYPE: PRT
<213> ORGANISM: Artificial Sequence
<220> FEATURE:
<223> OTHER INFORMATION: Synthetic Construct

<400> SEQUENCE: 6

Gly Ile Gly Asp Val Leu Lys Glu Leu Ala Asp Glu Leu Pro Ala Leu
1               5                   10                  15

Gln Glu Trp Ile His Ala Ala Gln Gln Leu
            20                  25

<210> SEQ ID NO 7
<211> LENGTH: 26
<212> TYPE: PRT
<213> ORGANISM: Artificial Sequence
<220> FEATURE:
<223> OTHER INFORMATION: Synthetic Construct

<400> SEQUENCE: 7

Gly Ile Gly Glu Val Leu Lys Asp Leu Ala Ala Glu Leu Pro Glu Leu
1               5                   10                  15

Gln Glu Trp Ile His Ala Ala Gln Gln Leu
            20                  25

<210> SEQ ID NO 8
<211> LENGTH: 26
<212> TYPE: PRT
<213> ORGANISM: Artificial Sequence
<220> FEATURE:
<223> OTHER INFORMATION: Synthetic Construct

<400> SEQUENCE: 8

Gly Ile Gly Glu Val Leu Lys Glu Leu Ala Asp Glu Leu Pro Glu Leu
1               5                   10                  15

Gln Glu Trp Ile His Ala Ala Gln Gln Leu
            20                  25

<210> SEQ ID NO 9
<211> LENGTH: 26
<212> TYPE: PRT
<213> ORGANISM: Artificial Sequence
```

```
<220> FEATURE:
<223> OTHER INFORMATION: Synthetic Construct

<400> SEQUENCE: 9

Gly Ile Gly Glu Val Leu His Glu Leu Ala Glu Gly Leu Pro Glu Leu
1               5                   10                  15

Gln Glu Trp Ile His Ala Ala Gln Gln Leu
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic Construct

<400> SEQUENCE: 10

Gly Ile Gly Glu Val Leu His Glu Leu Ala Asp Asp Leu Pro Glu Leu
1               5                   10                  15

Gln Ser Trp Ile Lys Ala Ala Gln Gln Leu
            20                  25

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct

<400> SEQUENCE: 11

Gly Ile Gly Asp Val Leu Lys Glu Leu Ala Glu Glu Leu Pro Leu Leu
1               5                   10                  15

Gln Glu Trp Ile Lys Ala Ala Gln Gln Leu
            20                  25

<210> SEQ ID NO 12
<211> LENGTH: 26
<212> TYPE: PRT
<213> ORGANISM: Artificial Sequence
<220> FEATURE:
<223> OTHER INFORMATION: Synthetic Construct

<400> SEQUENCE: 12

Gly Ile Gly Glu Val Leu Lys Asp Leu Ala Asp Leu Leu Pro Glu Leu
1               5                   10                  15

Gln Glu Trp Ile His Ala Ala Gln Gln Leu
            20                  25

<210> SEQ ID NO 13
<211> LENGTH: 26
<212> TYPE: PRT
<213> ORGANISM: Apis mellifera

<400> SEQUENCE: 13

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 14
<211> LENGTH: 26
<212> TYPE: PRT
<213> ORGANISM: Artificial Sequence
<220> FEATURE:
```

<223> OTHER INFORMATION: Synthetic Construct

<400> SEQUENCE: 14

Gly Ile Gly Ala Val Leu Lys Val Leu Ala Thr Gly Leu Pro Ala Leu
1               5                   10                  15

Ile Ser Trp Ile Lys Ala Ala Gln Gln Leu
            20                  25

<210> SEQ ID NO 15
<211> LENGTH: 26
<212> TYPE: PRT
<213> ORGANISM: Artificial Sequence
<220> FEATURE:
<223> OTHER INFORMATION: Synthetic Construct

<400> SEQUENCE: 15

Gly Ile Gly Ala Val Leu Lys Glu Leu Ala Asp Gly Leu Pro Ala Leu
1               5                   10                  15

Ile Asp Trp Ile Glu Ala Ala Gln Gln Leu
            20                  25

<210> SEQ ID NO 16
<211> LENGTH: 26
<212> TYPE: PRT
<213> ORGANISM: Artificial Sequence
<220> FEATURE:
<223> OTHER INFORMATION: Synthetic Construct

<400> SEQUENCE: 16

Gly Ile Gly Ala Val Leu Glu Glu Leu Ala Asp Asp Leu Pro Ala Leu
1               5                   10                  15

Ile Asp Trp Ile Glu Ala Ala Gln Gln Leu
            20                  25

<210> SEQ ID NO 17
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Ala, Leu, Asp, or Glu
<220> FEATURE:
<221> NAME/KEY: MISC_FEATURE
<222> LOCATION: (7)..(7)
<223> OTHER INFORMATION: Xaa is Lys or His
<220> FEATURE:
<221> NAME/KEY: MISC_FEATURE
<222> LOCATION: (8)..(8)
<223> OTHER INFORMATION: Xaa is Val, Asp, or Glu
<220> FEATURE:
<221> NAME/KEY: MISC_FEATURE
<222> LOCATION: (11)..(11)
<223> OTHER INFORMATION: Xaa is Thr, Ala, Asp, or Glu
<220> FEATURE:
<221> NAME/KEY: MISC_FEATURE
<222> LOCATION: (12)..(12)
<223> OTHER INFORMATION: Xaa is Gly, Leu, Asp, or Glu
<220> FEATURE:
<221> NAME/KEY: MISC_FEATURE
<222> LOCATION: (15)..(15)
<223> OTHER INFORMATION: Xaa is Ala, Leu, Asp, or Glu
<220> FEATURE:
<221> NAME/KEY: MISC_FEATURE
<222> LOCATION: (17)..(17)
<223> OTHER INFORMATION: Xaa is Ile or Gln
<220> FEATURE:
<221> NAME/KEY: MISC_FEATURE -continued

```
<222> LOCATION: (18)..(18)
<223> OTHER INFORMATION: Xaa is Ser, Asp, or Glu
<220> FEATURE:
<221> NAME/KEY: MISC_FEATURE
<222> LOCATION: (21)..(21)
<223> OTHER INFORMATION: Xaa is Lys or His

<400> SEQUENCE: 17

Gly Ile Gly Xaa Val Leu Xaa Xaa Leu Ala Xaa Xaa Leu Pro Xaa Leu
1               5                   10                  15

Xaa Xaa Trp Ile Xaa Ala Ala Gln Gln Leu
            20                  25

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Asp Tyr Lys Asp Asp Asp Asp Lys Gly
1               5
```

PORE-FORMING PEPTIDES AND USES THEREOF

STATEMENT REGARDING FEDERALLY SPONSORED RESEARCH

This invention was made with government support under Grant Nos. 1157687, 1003441, and 1003411 awarded by the National Science Foundation. The government has certain rights in the invention.

BACKGROUND OF THE INVENTION

Membrane-permeabilizing peptides can be used in a variety of biotechnological and clinical applications due to their ability to breach the barrier imposed by lipid bilayers (1-9). Such peptides may be designed to function only in specific environments or only in response to specific triggers. One potentially useful trigger is pH, which varies in spatially and temporally specific ways in cellular organelles and varies locally in tissues under some pathological conditions, including cancer (10-12). In one example application, pH-triggered membrane permeabilizing peptides may be triggered upon endosomal acidification to promote the release of uptaken polar molecules from endosomal compartments into the cell cytosol (1, 13-15). Such an application would eliminate a long-standing barrier to the ability to deliver generic polar compounds, especially proteins and other macromolecules, to cells (13, 16, 17). While efficient methods exist to deliver oligonucleotides to cells, most other types of macromolecules are more difficult to deliver. Useful macromolecules include, but are not limited to, proteins, such as antibodies, nanobodies, inhibitors, and enzymes, as well as peptides, polysaccharides, imaging agents, and other suitable macromolecules. These macromolecules can be directed to existing cellular uptake mechanisms (18, 19), but in the absence of endosome permeabilization or disruption, they often get trapped within the classical pathways that lead to their lysosomal degradation or recycling without significant entry into the cytosol (20, 21).

In a second example application, pH-sensitive, membrane permeabilizing peptides may be used in cancer therapies to selectively permeabilize the plasma membranes of cancer cells. This is possible because the environmental milieu in the vicinity of solid tumors is often acidic due to their high rate of mostly glycolytic metabolism (12). The locally acidic pH of solid tumors has previously been shown in mice to trigger the pH-sensitive insertion of peptides into membranes, but no evidence exists for peptides that cause permeabilization (10, 22).

Some progress has been made in the development of pH-triggered pore-forming peptides (23, 24) and other pH-triggered membrane active peptides (15, 25), including some that were designed rationally (26). The state-of-the art in the field has been trial and error-based addition of protonatable residues, such as aspartate (D), glutamate (E) and histidine (H). Two well-studied examples are pHLIP, which inserts across membranes at pH<5.5 without permeabilization, and GALA, which permeabilizes synthetic membranes at pH<5.5 (27). However, none of the known pH-sensitive peptides have all of the properties needed for the applications described above. For example, pHLIP does not form pores, although it can deliver small polar molecules that are covalently attached to it by insertion across the membrane (28). GALA, and others, are capable of forming pores in membranes, but these are only small pores (25, 27, 29-31) with limited utility for cellular delivery, especially for macromolecules.

For delivery of DNA and RNA, a major effort has been dedicated to developing strategies for bypassing endocytosis or causing release of macromolecules from endosomes prior to fusion with lysosomes. The use of cationic lipids (e.g. lipofectamine), cationic peptides, or cationic polymers (e.g. polyethylenimine (PEI)) for the delivery of DNA and RNA is widespread. The lipid-based approach relies on physical disruption of cell membranes. Peptide-based approaches utilize multiple mechanisms, including endosomal disruption. Polymer approaches rely mostly on the "proton sponge" effect in which endosomal acidification leads to polymer protonation, which in turn leads to counterion influx and osmotic lysis of endosomes. Newer, biodegradable polymers, such as poly ($\beta$-amino esters), also rely on this effect. Using these approaches, high efficiency for DNA transfection and siRNA delivery is now routine for many cell types and oligonucleotides. Yet for some cells, efficiencies remain low or undetectable (0-20%), and must be solved by trial and error for each cell type and cargo.

Importantly, there are also many classes of macromolecules with immense potential utility in the laboratory that cannot be delivered via complexation with cationic lipids, peptides, or polymers. For instance, a generic method for the cytosolic delivery of exogenous proteins, including, but not limited to, antibodies, nanobodies, or enzymes, to live cells, would have great utility in the laboratory. Thus, other classes of endosomal release agents are needed. Membrane-active peptides are potentially useful molecules for delivery of macromolecules. However, known examples of membrane-destabilizing peptides are cytolytic. Therefore, elaborate strategies have been tested with limited success to hide and/or deactivate them until they are endocytosed.

There exists literature on cell-penetrating peptides (CPPs), such as TAT, and on pH-sensitive peptides, such as GALA and pHLIP. However, the majority of these studies examine only the cellular entry of CPPs labeled with small molecule probes, rather than the delivery of macromolecular cargos. For example, in a large, curated database of CPPs, 95% of "cargoes" (excluding oligonucleotides) are small molecule probes; mostly fluorescein (60%) and biotin (25%) (43). Other than oligonucleotides, the known examples of macromolecule delivery typically require covalent attachment between the cargo and the delivery agent, which requires a unique synthesis or creates a molecular biology problem for every cargo and limits generalization.

A useful combination of properties would be pH-triggered membrane permeabilization that promotes the movement of macromolecules across membranes. Until recently, even non-triggered macromolecular poration activity that occurs at low peptide concentration has been rare or unknown in pore-forming peptides. Previously, high throughput screening of a peptide library was used to develop a peptide, designated MelP5, which allows macromolecules to pass through synthetic membranes even at very low concentration of peptide (32, 33). Thus, with MelP5, there is at least one sequence known that is a non-pH sensitive macromolecular pore forming peptide. And, as is discussed above, there are also sequences, such as GALA and pHLIP, which demonstrate pH sensitive membrane insertion and permeabilization without the ability to promote movement of macromolecules across membranes. There are no known sequences that have both properties. Thus, there exists a need for peptides that are pH sensitive, macromolecular pore-forming peptides.

SUMMARY OF THE INVENTION

The present invention discloses membrane permeabilizing peptides, polynucelotides encoding the peptides, compositions comprising the peptides, and methods for using the peptides and polynucelotides encoding the peptides in research, diagnosis, prevention, and treatment. This invention also relates to therapeutic, diagnostic, and preventative methods using membrane permeabilizing peptides and polynucelotides encoding the peptides. Preventative methods include preparation and use of vaccines and other compositions (e.g., lipid vesicles) containing, e.g., peptides and polynucleotides encoding the peptides, and, optionally, other factors (e.g., small molecules, peptides) that inhibit disease activity. Further, the invention features diagnostic and therapeutic compositions for the prevention and treatment of disease, including cancer. Also disclosed are new tools and methods for the design, production, and use of pH-sensitive, macromolecular pore-forming peptides and compositions comprising such peptides, including tools and methods for the development and production of reagents, diagnostics, vaccines, therapeutics, and screening tools.

One embodiment of the invention relates to membrane permeabilizing polypeptides and analogs, homologs, or fragments thereof, including membrane permeabilizing peptides that are sensitive to pH. The polypeptide may cause little or no membrane permeabilization at or above a predetermined pH value, such as about pH 7. The polypeptide may cause macromolecule passage across bilayers at or below a predetermined pH value, such as about pH 5. The polypeptide may comprise one or more D-amino acid peptides, which may be conjugated to one or more lipids. The one or more lipids may be selected from the group comprising laurate, myristate, palmitate, oleate, cholesterol or PEG-cholesterol.

Another embodiment of the invention relates to methods of producing or expressing membrane permeabilizing peptides and analogs, homologs, or fragments thereof, including membrane permeabilizing peptides that are sensitive to pH.

Another embodiment of the invention features nucleic acids containing one or more sequences encoding forms of membrane permeabilizing peptides and analogs, homologs, or fragments thereof, including membrane permeabilizing peptides that are sensitive to pH.

Another embodiment of the invention features expression vectors comprising polynucleotides encoding forms of membrane permeabilizing peptides and analogs, homologs, or fragments thereof, including membrane permeabilizing peptides that are sensitive to pH.

Another embodiment of the invention features fusion proteins containing membrane permeabilizing peptides and analogs, homologs, or fragments thereof, including membrane permeabilizing peptides that are sensitive to pH, that are linked to another polypeptide. Such other polypeptide may enhance the stability or immunogenicity of the membrane permeabilizing peptides, or may assist in the purification of said polypeptide. Such other polypeptide may be the FLAG-tag sequence (DYKDDDDKG), which facilitates purification through a FLAG affinity resin.

An embodiment of the invention features membrane permeabilizing peptides and analogs, homologs, or fragments thereof, including membrane permeabilizing peptides that are sensitive to pH, and diagnostic and/or therapeutic application of such peptides. The membrane permeabilizing peptides may comprise one or more D-amino acid peptides, which may be conjugated to one or more lipids. The one or more lipids may be selected from the group comprising laurate, myristate, palmitate, oleate, cholesterol or PEG-cholesterol.

Another embodiment of the invention features diagnostics comprising the membrane permeabilizing peptides and analogs, homologs, or fragments thereof, including membrane permeabilizing peptides that are sensitive to pH, and further including labeled peptides or fragments thereof of the invention.

Another embodiment of the invention features vaccines comprising the membrane permeabilizing peptides and analogs, homologs, or fragments thereof, including membrane permeabilizing peptides that are sensitive to pH.

Another embodiment of the invention features pharmaceutical compositions comprising the membrane permeabilizing peptides and analogs, homologs, or fragments thereof, including membrane permeabilizing peptides that are sensitive to pH. Such pharmaceutical composition may further comprise one or more pharmaceutically acceptable carriers and/or may be in the form of a lipid vesicle.

Another embodiment of the invention is directed to kits comprising the peptides of the invention.

Another embodiment of the invention is directed to therapeutics for preventing or treating disease in a patient comprising the peptides of the invention.

Another embodiment of the invention features methods of detecting disease using one or more of the peptides of the invention in a sample obtained from a subject suspected of having disease.

Another embodiment of the invention features methods of treating or preventing disease in a subject (e.g., a human) comprising administering one or more of the peptides of the invention to said subject (e.g., in the form of a lipid vesicle containing such peptides or polynucleotides encoding such peptides).

Other embodiments and advantages of the invention are set forth in part in the description, which follows, and in part, may be obvious from this description, or may be learned from the practice of the invention.

In one aspect, the invention features an isolated polypeptide having at least 85% (e.g., 90%, 95%, 97%, 99%, or 100%) sequence identity to the sequence of any one of SEQ ID NOs: 1-12. The polypeptide may have the sequence of the sequence of SEQ ID NO: 2. The polypeptide does not have the sequence of any one of SEQ ID NOs: 13-16. The polypeptide may form a pore at a pH of less than about pH 7.0.

The polypeptide may be conjugated to a lipid (e.g., laurate, myristate, palmitate, oleate, cholesterol, and PEG-cholesterol). The polypeptide may further comprise one or more D-amino acids (e.g., D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL). The polypeptide may further comprise one or more derivatized amino acids (e.g., N-imbenzylhistidine, 4-hydroxyproline, 5-hydroxylysine, 3-methylhistidine, homoserine, and ornithine). The derivatized amino acid may have a chemical moiety selected from the group consisting of amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl.

In another aspect, the invention features a polynucleotide encoding the polypeptide of any of the above aspects.

In another aspect, the invention features a vector including the polynucleotide encoding the polypeptide of any of the above aspects.

In another aspect, the invention features a chimeric protein including the polypeptide of any of the above aspects linked (e.g., covalently) to a second polypeptide. The second polypeptide may enhance stability or immunogenicity of the polypeptide. The second polypeptide may facilitate purification of the polypeptide, such as is achieved by, e.g., a FLAG tag.

In another aspect, the invention features a lipid bilayer including the polypeptide or chimeric protein of any of the above aspects. The lipids may be phospholipids. In another aspect, the invention features a lipid vesicle including the lipid bilayer. The lipid vesicle may further comprise a cargo (e.g., a therapeutic agent, such as a cancer therapeutic agent) within (e.g., encapsulated within) the lipid vesicle.

In some embodiments, the cancer therapeutic agent is selected from the group consisting of Abiraterone Acetate, ABITREXATE® (Methotrexate), ABRAXANE® (Paclitaxel Albumin), ADCETRIS® (Brentuximab Vedotin), ado-trastuzumab emtansine, ADRIAMYCIN® (doxorubicin hydrochloride), afatinib dimaleate, AFINITOR® (Everolimus), AKYNZEO® (netupitant and palonosetron hydrochloride), ALDARA® (imiquimod), aldesleukin, ALECENSA® (alectinib), alectinib, alemtuzumab, ALKERAN® for Injection (Melphalan Hydrochloride), ALKERAN® tablets (melphalan), ALIMTA® (pemetrexed disodium), ALOXI® (palonosetron hydrochloride), AMBOCHLORIN® (chlorambucil), AMBOCLORIN® (Chlorambucil), aminolevulinic acid, anastrozole, aprepitant, AREDIA® (pamidronate disodium), ARIMIDEX® (anastrozole), AROMASIN® (exemestane), ARRANON® (nelarabine), arsenic trioxide, ARZERRA® (ofatumumab), asparaginase *Erwinia chrysanthemi*, AVASTIN® (bevacizumab), axitinib, azacitidine, BELEODAQ® (Belinostat), belinostat, bendamustine hydrochloride, bevacizumab, bexarotene, BEXXAR® (tositumomab and iodine $^{131}$I tositumomab), bicalutamide, BiCNU (carmustine), bleomycin, blinatumomab, BLINCYTO® (blinatumomab), bortezomib, BOSULIF® (bosutinib), bosutinib, brentuximab vedotin, busulfan, BUSULFEX® (busulfan), cabazitaxel, cabozantinib-S-malate, CAMPATH® (alemtuzumab), CAMPTOSAR® (irinotecan hydrochloride), capecitabine, CARAC® (fluorouracil), carboplatin, CARBOPLATIN-TAXOL®, carfilzomib, CARMUBRIS® (carmustine), carmustine, carmustine implant, CASODEX® (bicalutamide), CEENU (lomustine), ceritinib, CERUBIDINE® (daunorubicin hydrochloride), CERVARIX® (recombinant HPV bivalent vaccine), cetuximab, chlorambucil, chlorambucil-prednisone, cisplatin, CLAFEN® (cyclophosphamide), clofarabine, CLOFAREX® (clofarabine), CLOLAR® (Clofarabine), cobimetinib, cometriq (cabozantinib-S-malate), COSMEGEN® (dactinomycin), COTELLIC® (cobimetinib), crizotinib, cyclophosphamide, CYFOS® (ifosfamide), CYRAMZA® (ramucirumab), cytarabine, cytarabine liposome, CYTOSAR-U® (cytarabine), CYTOXAN® (cyclophosphamide), dabrafenib, dacarbazine, DACOGEN® (decitabine), dactinomycin, daratumumab, DARZALEX® (daratumumab), dasatinib, daunorubicin hydrochloride, decitabine, degarelix, denileukin diftitox, denosumab, DEPOCYT® (cytarabine liposome), dexamethasone, dexrazoxane hydrochloride, dinutuximab, docetaxel, DOXIL® (doxorubicin hydrochloride), doxorubicin hydrochloride, DOX-SL® (doxorubicin hydrochloride), DTIC-DOME® (dacarbazine), EFUDEX (fluorouracil), ELITEK® (rasburicase), ELLENCE® (epirubicin hydrochloride), elotuzumab, ELOXATIN® (oxaliplatin), eltrombopag olamine, EMEND® (aprepitant), EMPLICITI® (elotuzumab), enzalutamide, epirubicin hydrochloride, ERBITUX® (cetuximab), eribulin mesylate, ERIVEDGE® (vismodegib), erlotinib hydrochloride, ERWINAZE® (asparaginase *Erwinia chrysanthemi*), ETOPOPHOS® (etoposide phosphate), etoposide, etoposide phosphate, EVACET® (doxorubicin hydrochloride liposome), everolimus, EVISTA® (raloxifene hydrochloride), EVOMELA® (melphalan hydrochloride), exemestane, 5-FU (5-fluorouracil), FARESTON® (toremifene), FARYDAK® (panobinostat), FASLODEX® (fulvestrant), FEMARA® (letrozole), filgrastim, FLUDARA® (fludarabine phosphate), fludarabine phosphate, FLUOROPLEX® (fluorouracil), fluorouracil injection, flutamide, FOLEX® (methotrexate), FOLEX® PFS (methotrexate), fulvestrant, GARDASIL® (recombinant HPV quadrivalent vaccine), GARDASIL 9® (recombinant HPV nonavalent vaccine), GAZYVA® (obinutuzumab), gefitinib, gemcitabine hydrochloride, gemcitabine-cisplatin, gemcitabine-oxaliplatin, gemtuzumab ozogamicin, GEMZAR® (gemcitabine hydrochloride), GILOTRIF® (afatinib dimaleate), GLEEVEC® (imatinib mesylate), GLIADEL® (carmustine implant), GLIADEL® wafer (carmustine implant), glucarpidase, goserelin acetate, HALAVEN® (eribulin mesylate), HERCEPTIN® (trastuzumab), HPV bivalent vaccine, HYCAMTIN® (topotecan hydrochloride), IBRANCE (palbociclib), IBRITUMOMAB® tiuxetan, ibrutinib, ICLUSIG® (ponatinib hydrochloride), IDAMYCIN® (idarubicin hydrochloride), idarubicin hydrochloride, idelalisib, IFEX® (ifosfamide), ifosfamide, ifosfamidum, IL-2 (aldesleukin), imatinib mesylate, IMBRUVICA® (ibrutinib), ilmiquimod, IMLYGIC® (talimogene laherparepvec), INLYTA (axitinib), recombinant interferon alpha-2b, intron A, tositumomab, such as $^{131}$I tositumomab, ipilimumab, IRESSA® (gefitinib), irinotecan hydrochloride, ISTODAX® (romidepsin), ixabepilone, ixazomib citrate, IXEMPRA® (ixabepilone), JAKAFI® (ruxolitinib phosphate), JEVTANA® (cabazitaxel), KADCYLA® (ado-trastuzumab emtansine), KEOXIFENE® (raloxifene hydrochloride), KEPIVANCE® (palifermin), KEYTRUDA® (pembrolizumab), KYPROLIS® (carfilzomib), lanreotide acetate, lapatinib ditosylate, lenalidomide, lenvatinib mesylate, LENVIMA® (lenvatinib mesylate), letrozole, leucovorin calcium, leukeran (chlorambucil), leuprolide acetate, levulan (aminolevulinic acid), LINFOLIZIN® (chlorambucil), LIPODOX® (doxorubicin hydrochloride liposome), lomustine, LONSURF® (trifluridine and tipiracil hydrochloride), LUPRON® (leuprolide acetate), LYNPARZA® (olaparib), MARQIBO® (vincristine sulfate liposome), MATULANE® (procarbazine hydrochloride), mechlorethamine hydrochloride, megestrol acetate, MEKINIST® (trametinib), melphalan, melphalan hydrochloride, mercaptopurine, MESNEX® (mesna), METHAZOLASTONE® (temozolomide), methotrexate, methotrexate LPF, MEXATE® (methotrexate), MEXATE-AQ® (methotrexate), mitomycin C, mitoxantrone hydrochloride, MITOZYTREX® (mitomycin C), MOZOBIL® (plerixafor), MUSTARGEN® (mechlorethamine hydrochloride), MUTAMYCIN® (mitomycin C), MYLERAN® (busulfan), MYLOSAR® (azacitidine), MYLOTARG® (gemtuzumab ozogamicin), nanoparticle paclitaxel, NAVELBINE® (vinorelbine tartrate), NECITUMUMAB, nelarabine, NEOSAR® (cyclophosphamide), netupitant and palonosetron hydrochloride, NEUPOGEN® (filgrastim), NEXAVAR® (sorafenib tosylate), NILOTINIB, NINLARO® (ixazomib citrate), nivolumab, NOLVADEX® (tamoxifen citrate), NPLATE® (romiplostim), obinutuzumab, ODOMZO® (sonidegib), ofatumumab, olaparib, omacetaxine mepesuccinate, ONCASPAR® (pegaspargase), ondansetron hydrochloride, ONIVYDE® (irinotecan hydrochloride liposome), ONTAK® (denileukin diftitox), OPDIVO® (nivolumab), osimertinib, oxaliplatin, paclitaxel, paclitaxel albumin-stabilized nanoparticle formulation, palbociclib, palifermin, palonosetron hydrochloride, palonosetron hydrochloride and netupitant, pamidronate disodium, panitumumab, panobinostat, PARAPLAT® (carboplatin), PARPLATIN® (carboplatin), pazopanib hydrochloride, pegaspargase, peginterferon alpha-2b, PEG-INTRON® (peginterferon alpha-2b), pembrolizumab, pemetrexed disodium, PERJETA® (pertuzumab), pertuzumab, PLATINOL® (cisplatin), PLATINOL-AQ® (cisplatin), plerixafor, pomalidomide, POMALYST® (pomalidomide), ponatinib hydrochloride, PORTRAZZA® (necitumumab), pralatrexate, prednisone, procarbazine hydrochloride, PROLEUKIN® (aldesleukin), PROLIA® (denosumab), PROMACTA (eltrombopag olamine), PROVENGE® (sipuleucel-T), PURINETHOL® (mercaptopurine), PURIXAN® (mercaptopurine), $^{223}$Ra dichloride, raloxifene hydrochloride, ramucirumab, rasburicase, recombinant human papillomavirus (HPV), recombinant interferon alpha-2b, regorafenib, REVLIMID® (lenalidomide), RHEUMATREX® (methotrexate), RITUXAN® (rituximab), rolapitant hydrochloride, romidepsin, romiplostim, rubidomycin (daunorubicin hydrochloride), ruxolitinib phosphate, SCLEROSOL® intrapleural aerosol (talc), siltuximab, sipuleucel-T, somatuline depot (lanreotide acetate), sonidegib, sorafenib tosylate, SPRYCEL® (dasatinib), sterile talc powder (talc), STERITALC® (talc), STIVARGA® (regorafenib), sunitinib malate, SUTENT® (sunitinib malate), SYLATRON® (peginterferon alpha-2b), SYLVANT® (siltuximab), SYNOVIR® (thalidomide), SYNRIBO® (omacetaxine mepesuccinate), thioguanine, TAFINLAR® (dabrafenib), TAGRISSO® (osimertinib), talimogene laherparepvec, tamoxifen citrate, tarabine PFS (cytarabine), TARCEVA (erlotinib hydrochloride), TARGRETIN® (bexarotene), TASIGNA® (nilotinib), TAXOL® (paclitaxel), TAXOTERE® (docetaxel), TEMODAR® (temozolomide), temsirolimus, thalidomide, THALOMID® (thalidomide), thioguanine, thiotepa, TOLAK® (topical fluorouracil), topotecan hydrochloride, toremifene, TORISEL® (temsirolimus), TOTECT® (dexrazoxane hydrochloride), rabectedin, trametinib, TREANDA® (bendamustine hydrochloride), trifluridine and tipiracil hydrochloride, TRISENOX® (arsenic trioxide), TYKERB® (lapatinib ditosylate), UNITUXIN® (dinutuximab), uridine triacetate, vandetanib, VARUBI® (rolapitant hydrochloride), vectibix (panitumumab), VELBAN® (vinblastine sulfate), VELCADE® (bortezomib), VELSAR (vinblastine sulfate), VEMURAFENIB, VIADUR (leuprolide acetate), VIDAZA (azacitidine), vinblastine sulfate, VINCASAR® PFS (vincristine sulfate), vincristine sulfate, vinorelbine tartrate, vismodegib, VISTOGARD® (uridine triacetate), VORAXAZE® (glucarpidase), vorinostat, VOTRIENT® (pazopanib hydrochloride), WELLCOVORIN® (leucovorin calcium), XALKORI® (crizotinib), XELODA® (capecitabine), XGEVA® (denosumab), XOFIGO® ($^{223}$Ra dichloride), XTANDI® (enzalutamide), YERVOY® (ipilimumab), YONDELIS® (trabectedin), ZALTRAP® (ziv-aflibercept), ZARXIO® (filgrastim), ZELBORAF® (vemurafenib), ZEVALIN® (ibritumomab tiuxetan), ZINECARD® (dexrazoxane hydrochloride), ziv-aflibercept, ZOFRAN® (ondansetron hydrochloride), ZOLADEX® (gGoserelin acetate), zoledronic acid, ZOLINZA® (vorinostat), ZOMETA® (zoledronic acid), ZYDELIG® (idelalisib), ZYKADIA® (ceritinib), and ZYTIGA (abiraterone acetate), or is selected from the following combinations of agents: ADRIAMYCIN®, bleomycin, vinblastine, and dacarbazine (ABVD); ADRIAMYCIN®, bleomycin, vincristine sulfate, and etoposide phosphate (ABVE); ADRIAMYCIN®, bleomycin, vincristine sulfate, etoposide phosphate, prednisone, and cyclophosphamide (ABVE-PC); doxorubicin and cyclophosphamide (AC); doxorubicin, cyclophosphamide, and paclitaxel or docetaxel (ACT); cytarabine (Ara-C), daunorubicin, and etoposide (ADE); cyclophosphamide, doxorubicin hydrochloride, vincristine sulfate, and prednisone (CHOP); etoposide phosphate, prednisone, vincristine sulfate (Oncovin), cyclophosphamide, and doxorubicin hydrochloride (hydroxydaunorubicin) (EPOCH); rituximab, etoposide phosphate, prednisone, vincristine sulfate (oncovin), cyclophosphamide, and doxorubicin hydrochloride (hydroxydaunorubicin) (R-EPOCH); folinic acid, fluorouracil, and irinotecan (FOLIFIRI); FOLFIRI-bevacizumab; FOLFIRI-cetuximab; folinic acid, fluorouracil, irinotecan, and oxaliplatin (FOLIFIRINOX); folinic acid, fluorouracil, and oxaliplatin (FOLFOX); FOLOTYN® (pralatrexate), fluorouracil and leucovorin (FU-LV); rituximab, ifosfamide, carboplatin, etoposide (ICE); rituximab, cyclophosphamide, doxorubicin hydrochloride, vincristine sulfate, and prednisone (R-CHOP); irinotecan and capecitabine (XELIRI); oxaliplatin and capecitabine (XELOX); bleomycin, etoposide, Adriamycin, cyclophosphamide, oncovin, procarbazine, prednisone (BEACOPP); bleomycin, etoposide, and cisplatin (BEP); cyclophosphamide, doxorubicin, and 5-Fluorouracil (CAF); capecitabine and oxaliplatin (CAPDX); cisplatin, etoposide, and methotrexate (CEM); cyclophosphamide, methotrexate, and fluorouracil (CMF); cyclophosphamide, oncovin, prednisone, and dacarbazine (COPDAC); cyclophosphamide, oncovin, procarbazine hydrochloride, and prednisone (COPP); COPP, Adriamycin, bleomycin, and vinblastine sulfate (COPP-ABV); cyclophosphamide, vincristine, and prednisolone (CVP); 5'-fluorouracil, epirubicin, cyclophosphamide (FEC); hyper cyclophosphamide, vincristine, adriamycin (hyper-CVAD); mutargen, oncovin, procarbazine, and prednisone (MOPP); oncovin, etoposide phosphate, prednisone, and Adriamycin (OEPA); oxaliplatin, fluorouracil, and leucovorin (OFF); oncovin, prednisone, procarbazine hydrochloride, and Adriamycin (OPPA); bortezomib, dexamethasone, and doxorubicin (PAD); procarbazine, lomustine, and vincristine (PCV); rituximab, cyclophosphamide, vincristine sulfate, and prednisone (R-CVP); doxorubicin, vinblastine, mechlorethamine, vincristine, bleomycin, etoposide, and prednisone (STANFORD V); docetaxel, Adriamycin, and cyclophosphamide (TAC); taxotere, platinol, and fluorouracil (TPF); vincristine sulfate, actinomycin-D, and cyclophosphamide (VAC); vincristine, amethopterine, methotrexate, and prednisone (VAMP); vincristine sulfate, etoposide, L-asparaginase, and prednisone acetate (VELP); and vepesid, ifosfamide, and platinol (VIP).

In some embodiments, the lipid vesicle further comprises a targeting molecule. The targeting molecule may be a receptor, a receptor ligand, an antibody or antigen-binding fragment thereof (e.g., an scFv), or a combination thereof. The targeting molecule may bind to a cancer cell.

In some embodiments, the cancer is selected from the group consisting of leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

In some embodiments, the targeting molecule binds to a tumor associated antigen (TAA), e.g., a TAA selected from the group of TAAs listed in Table 2.

In another aspect, the invention features a method of delivering a cargo (e.g., a therapeutic agent, such as a cancer therapeutic agent) to a target cell (e.g., a cancer cell), by contacting the target cell with the lipid vesicle of any of the above aspects.

In another aspect, the invention features a method of treating cancer in a subject (e.g., a human) in need thereof by administering a lipid vesicle of any of the above aspects to the subject, e.g., in an amount and/or for a duration sufficient to treat the cancer.

In some embodiments, the cargo is delivered to the target cell when the pH drops below a predetermined threshold (e.g., about pH 4.0 to about pH 7.5, such as about pH 4.5, 5.0, 5.5, 6.0, and 7.0)

The cancer may be leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

In another aspect, the invention features a method of permeabilizing a membrane by contacting the membrane with a polypeptide described herein (e.g., a polypeptide having at least 85% (e.g., 90%, 95%, 97%, 99%, or 100%) sequence identity to the sequence of any one of SEQ ID NOs: 1-12), a chimeric protein containing the polypeptide, a lipid bilayer containing the polypeptide, or a lipid vesicle containing the polypeptide or a polynucleotide encoding the polypeptide of any of the above aspects. The method may further comprise lowering a pH at the membrane to a pH below about pH 7.0.

In another aspect, the invention features a lipid vesicle in accordance with any of the above aspects for use in treating a disease (e.g., cancer) in a subject (e.g., a human). The cancer may be leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

In another aspect, the invention features a kit comprising a composition of any of the above aspects (e.g., a polypeptide described herein (e.g., a polypeptide having at least 85% (e.g., 90%, 95%, 97%, 99%, or 100%) sequence identity to the sequence of any one of SEQ ID NOs: 1-12), a chimeric protein containing the polypeptide, a lipid bilayer containing the polypeptide, or a lipid vesicle containing the polypeptide or a polynucleotide encoding the polypeptide).

Definitions

As used herein, the term "about" refers to a value that is no more than 10% above or below the value being described. For example, the term "about pH 7" indicates a range of from pH 6.3 to pH 7.7.

As used herein, the term "acidic amino acid" refers to an amino acid having a side chain containing a carboxylic acid group having a pKa between 3.5 and 4.5. Acidic amino acids are aspartic acid and glutamic acid.

As used herein, the term "basic amino acid" refers to an amino acid whose side chain contains an amino group having a pKa between 9.5 and 13. Basic amino acids are histidine, lysine, and arginine. The term "analog" includes any polypeptide having an amino acid residue sequence substantially identical to a polypeptide of the invention in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; and the substitution of one acidic residue, such as aspartic acid or glutamic acid or another. The phrase conservative substitution also includes the use of a chemically derivatized residue in place of a non-derivatized residue.

The term "chemical derivative" refers to a subject polypeptide having one or more amino acid residues chemically derivatized by reaction of a functional side group. Examples of such derivatized amino acids include for example, those amino acids in which free amino groups have been derivatized to form amine hydrochlorides, p-toluene sulfonyl groups, carbobenzoxy groups, t-butyloxycarbonyl groups, chloroacetyl groups or formyl groups. Also, the free carboxyl groups of amino acids may be derivatized to form salts, methyl and ethyl esters or other types of esters or hydrazides. Also, the free hydroxyl groups of certain amino acids may be derivatized to form O-acyl or O-alkyl derivatives. Also, the imidazole nitrogen of histidine may be derivatized to form N-imbenzylhistidine. Also included as chemical derivatives are those proteins or peptides which contain one or more naturally occurring amino acid derivatives of the twenty standard amino acids. For example, 4-hydroxyproline may be substituted for proline, 5-hydroxylysine may be substituted for lysine, 3-methylhistidine may be substituted for histidine, homoserine may be substituted for serine, and ornithine may be substituted for lysine. Polypeptides of the present invention also include any polypeptide having one or more additions and/or deletions of residues relative to the sequence of any one of the polypeptides whose sequence is described herein.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c means that the process includes at least steps a, b and c. Wherever the terms "a" or "an" are used, "one or more" is understood, unless such interpretation is nonsensical in context.

As used herein, the term "duration" refers to the length of time or a timecourse over which a therapeutic agent (e.g., a peptide described herein or a composition containing such a peptide, or polynucleotide encoding such a peptide) is administered.

As used herein, the term "nonpolar amino acid" refers to an amino acid having relatively low-water solubility. Nonpolar amino acids are glycine, leucine, isoleucine, alanine, phenylalanine, methionine, tryptophan, valine, and proline.

As used herein, the term "percent (%) identity" refers to the percentage of amino acid residues of a candidate sequence, e.g., a mutant Melittin polypeptide, that are identical to the amino acid residues of a reference sequence, e.g., a wild-type Melittin polypeptide, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

$$100 \times (\text{fraction of A/B})$$

where A is the number of amino acid residues scored as identical in the alignment of the candidate sequence and the reference sequence, and where B is the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 15 contiguous positions, about 20 contiguous positions, about 25 contiguous positions, or more (e.g., about 30 to about 75 contiguous positions, or about 40 to about 50 contiguous positions, in which a sequence may be compared to a reference sequence of the same number of contiguous positions after the two sequences are optimally aligned.

As used herein, the term "pharmaceutically acceptable carrier" refers to an excipient or diluent in a pharmaceutical composition. The pharmaceutically acceptable carrier is compatible with the other ingredients of the formulation and not deleterious to the recipient. The pharmaceutically acceptable carrier may provide pharmaceutical stability to the pore forming polypeptide or may impart another beneficial characteristic (e.g., sustained release characteristics). The nature of the carrier differs with the mode of administration. For example, for intravenous administration, an aqueous solution carrier is generally used; for oral administration, a solid carrier is preferred.

As used herein, the term "pharmaceutical composition" refers to a medicinal or pharmaceutical formulation that contains an active ingredient at a pharmaceutically acceptable purity as well as one or more excipients and diluents to enable the active ingredient suitable for the method of administration. The pharmaceutical composition includes pharmaceutically acceptable components that are compatible with, for example, a pore forming polypeptide. The pharmaceutical composition may be in aqueous form, for example, for intravenous or subcutaneous administration or in tablet or capsule form, for example, for oral administration.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids are serine, threonine, cysteine, histidine, methionine, tyrosine, tryptophan, asparagine, and glutamine.

As used herein, the term "subject" refers to a mammal, e.g., a human.

As used herein, the term "therapeutically effective amount" refers to an amount, e.g., a pharmaceutical dose, effective in inducing a desired biological effect in a subject or patient or in treating a patient having a condition or disorder described herein (e.g., cancer). It is also to be understood herein that a "therapeutically effective amount" may be interpreted as an amount giving a desired therapeutic effect, either taken in one dose or in any dosage or route, taken alone or in combination with other therapeutic agents.

As used herein, the terms "treatment" or "treating" refer to reducing or ameliorating a disorder and/or symptoms associated therewith (e.g., cancer). It will be appreciated that, although not precluded, treating a disorder or condition does not require that the disorder or symptoms associated therewith be completely eliminated. Reducing or decreasing the side effects of a disease or condition, such as cancer, or the risk or progression of the disease or condition, may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement.

Wherever any of the phrases "for example," "such as," "including" and the like are used herein, the phrase "and without limitation" is understood to follow unless explicitly stated otherwise. Similarly, "an example," "exemplary" and the like are understood to be non-limiting. The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

BRIEF DESCRIPTION OF THE DRAWINGS

FIGS. 1A-1C are a set of schematic designs of an iterative peptide library. The library is shown in helical wheel (FIG. 1A) and space-filling representations (FIG. 1B). The library was based on the non pH-sensitive macromolecular poreformer MelP5, which is the sequence shown. Residue shape indicates type, with triangles representing hydrophobic residues and triangles representing polar residues, for example. Possible variations are shown at the bottom. Grey positions could be the native residue, or aspartate or glutamate. In some cases, a fourth hydrophobic residue was also possible. Black residues are lysine in MelP5 and may be lysine or histidine in the library members. Position 17 may have the native hydrophobic isoleucine or a polar glutamine. The most important aspect of the library is in the incorporation of protonatable acidic residues that align along one face of the helix, as shown. FIG. 1C depicts the consensus sequence.

FIGS. 2A-2B are a set of schematic drawings showing two different leakage assays that were used to measure the pore-forming activity of the peptides and screen for the desired activities. FIG. 2A: To evaluate leakage of small molecules, ANTS, a small molecule dye, was co-encapsulated with DPX, its obligate quencher, inside lipid vesicles (39). Membrane destabilization results in release of ANTS and DPX and recovery of ANTS fluorescence. FIG. 2B: To evaluate leakage of macromolecules, a recently published assay (33) based on FRET detection was used. Here, a 40 kDa dextran co-labelled with biotin and the acceptor fluorophore, TAMRA, is encapsulated within vesicles. Streptavidin labeled with the donor fluorophore, AlexaFluor488, is on the outside of the vesicles. Upon macromolecular permeation, the TAMRA-biotin-dextran (TBD) can escape where it complexes with streptavidin, allowing FRET to occur. In the presently-disclosed high-throughput screen, leakage of ANTS/DPX was measured at pH 7 and nominal P:L=1:200 and leakage of TBD at pH 5 and nominal P:L=1:800.

FIG. 4A: Macromolecule leakage versus pH. A representative set of positive peptides from Table 1 were synthesized and assessed for their ability to promote leakage of a 40,000 Da TBD (FIG. 2B) at P:L=1:200 and 1 mM POPC vesicles. Changes in pH lead to sharp transition in macromolecular poration. The apparent pKa values from the curve midpoints range from 5.5 to 5.8. FIG. 4B: Macromolecule leakage versus concentration. The peptides were assessed for their ability to promote leakage of a 40,000 Da TBD (FIG. 2B) at pH 5 and pH 7. The peptides exhibit no activity at pH 7, as desired, even at peptide to lipid ratios as high as 1:50 (dashed lines). At pH 5, all peptides transition from inactive at P:L<<0.001 to causing 100% TBD release between P:L=1:700 and P:L=1:200. Curve midpoints range from P:L ~1:900 to ~1:600.

FIG. 5A: Circular dichroism spectra of pHD108 (SEQ ID NO: 9) versus pH at P:L=1:200 in 1 mM POPC vesicles. Separate samples are made at each pH and equilibrated for 30 minutes prior to the measurement. The spectra show a structural transition from random coil at pH 7 to classical α-helix at pH<5.75. FIG. 5B: Tryptophan fluorescence spectra of pHD108 at P:L=1:200 in 1 mM POPC vesicles. Separate samples are made at each pH and equilibrated for 30 minutes prior to the measurement. The spectra show a transition from a more polar, water-exposed environment to a less polar or buried environment consistent with peptide partitioning into bilayers.

FIG. 6A), pHD24 (SEQ ID NO: 4; FIG. 6B), and pHD108 (SEQ ID NO: 9; FIG. 6C), changes in TBD leakage, changes in α-helicity from CD and changes in tryptophan fluorescence as pH is varied were plotted. All measurements are at P:L=1:200. Curves represent the global fit for each peptide of a cooperative transition using all three data sets. Tryptophan fluorescence spectra are corrected for the effect of pH on the intensity of free tryptophan. There is little or no detectable difference between leakage, structure and binding, consistent with the hypothesis that they are coupled.

DETAILED DESCRIPTION

Figure 3:
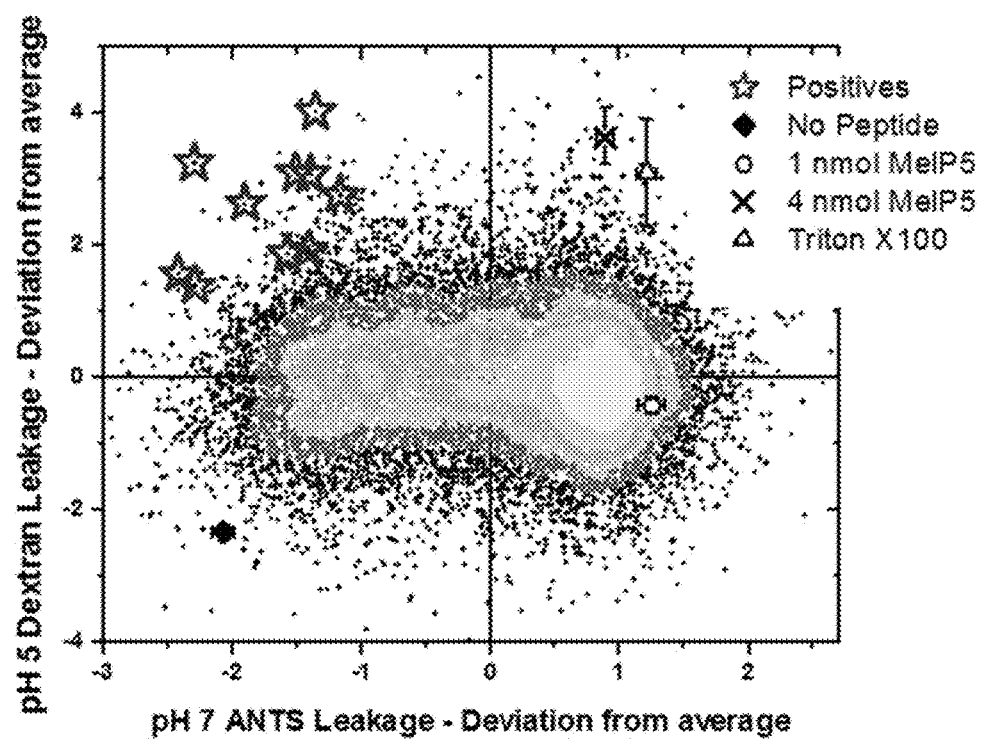
FIG. 3 is a plot showing the results of the screen. The serial, two part screen described in FIG. 2 was used to assay 15,000 randomly selected library members. The two activities for each of the 15,000 library members are shown as points on a temperature scale, where the point color is determined by point density, from light grey (most dense) to black (least dense). The results of each assay are shown as Z-values, or the difference of each point from the plate mean expressed as standard deviations. This approach normalizes for batch-to-batch variations in lipid vesicle intensities in the two assays. About 0.5 nmol of each library member was assayed. For comparison, values are shown for 1 and 4 nmol MelP5, for Triton-X-100 detergent, which solubilizes vesicles, and for buffer only. The center of the light grey area corresponds to ~85% ANTS leakage and ~30% dextran leakage. Most library members are similar to the template MelP5, but there are outliers in all four quadrants. The peptides of interest with low ANTS leakage at pH 7 and P:L=1:200 and high TBD release at pH 5 and P:L=1:800 are found in the upper left corner. Ten positive sequences, highlighted with stars, were selected and sequenced using Edman degradation. Their sequences are shown in Table 1.

Described herein are membrane permeabilizing peptides, polynucleotides encoding the peptides, and methods for using these peptides in research, diagnosis, prevention, and treatment. Specifically provided are pH-sensitive, macromolecular pore-forming peptides and compositions, such as lipid bilayers and lipid vesicles, containing such peptides, e.g., for development and production of reagents, diagnostics, vaccines, therapeutics, and screening tools.

We have used a high-throughput approach to discover pH-sensitive, macromolecular pore-forming peptides. First, the sequence of the macromolecular pore former, MelP5 and sequence features found in GALA and pHLIP were used to design a rational combinatorial peptide library. An orthogonal high-throughput screen was then developed to identify sequences from the library that have the following two properties in synthetic bilayers: (i) little membrane permeabilization at physiological pH 7 at high peptide concentration (e.g., above a threshold concentration at which the peptide spontaneously forms a macromolecular structure at neutral pH) and (ii) efficient formation of macromolecule-sized defects (e.g., a pore sized to allow passage of a molecule having a molecular weight of 1 Da-100,000 kDa (e.g., 1 Da, 2 Da, 3 Da, 4 Da, 5 Da, 6 Da, 7 Da, 8 Da, 9 Da, 10 Da, 20 Da, 30 Da, 40 Da, 50 Da, 60 Da, 70 Da, 80 Da, 90 Da, 100 Da, 200 Da, 300 Da, 400 Da, 500 Da, 600 Da, 700 Da, 800 Da, 900 Da, 1 kDa, 2 kDa, 3 kDa, 4 kDa, 5 kDa, 6 kDa, 7 kDa, 8 kDa, 9 kDa, 10 kDa, 20 kDa, 30 kDa, 40 kDa, 50 kDa, 60 kDa, 70 kDa, 80 kDa, 90 kDa, 100 kDa, 200 kDa, 300 kDa, 400 kDa, 500 kDa, 600 kDa, 700 kDa, 800 kDa, 900 kDa, 1,000 kDa, 2,000 kDa, 3,000 kDa, 4,000 kDa, 5,000 kDa, 6,000 kDa, 7,000 kDa, 8,000 kDa, 9,000 kDa, 10,000 kDa, 20,000 kDa, 30,000 kDa, 40,000 kDa, 50,000 kDa, 60,000 kDa, 70,000 kDa, 80,000 kDa, 90,000 kDa, 100,000 kDa) in membranes at acidic pH 5 and low peptide concentration (e.g., a peptide to lipid (P:L) ratio of about 1:100, 1:150, 1:200, 1:250, 1:300, 1:350, 1:400, 1:450, 1:500, 1:550, 1:600, 1:650, 1:700, 1:750, 1:800, 1:850, 1:900, 1:950, 1:1000, 1:1100, 1:1200, 1:1500, 1:2000, or more, or below a threshold concentration (e.g., a concentration of about 1 mM to about 0.001 nM (e.g., about 500 μM to about 1 nM, such as about 100 μM, about 50 μM, about 20 μM, about 10 μM, about 5 μM about 2.5 μM, about 1.0 μM, 0.5 μM, about 0.1 μM, about 0.05 μM, about 0.01 μM, about 1 nM, about 0.01 nM, and about 0.001 nM), e.g., a threshold concentration at which the peptide spontaneously forms a macromolecular structure, e.g., at neutral pH). Such peptides will have no effect on membranes at normal cellular pH but will be triggered at a physiologically acidic pH (e.g., pH<7) to form macromolecule-sized pores. This approach led to the development of a conserved motif for pH-triggered, macromolecule sized poration. Peptides having this motif can be embedded in lipid bilayers or lipid vesicles and functionally triggered to form assemble into a pore by a change in pH. The ability to modulate pH to trigger the formation of a pore offers uses in multiple biotechnological and pharmaceutical applications as described herein.

Polypeptides

Featured are membrane permeabilizing polypeptides, such as polypeptides that exhibit the ability to form pores that promote movement of macromolecules (e.g., small molecules, such as cancer therapeutic agents), in response to a change in pH (e.g., at a pH below about pH 7.0 (e.g., at about pH 5.0)). The term polypeptide is used broadly herein to include peptides, proteins or fragments thereof. By way of example and not limitation, a membrane permeabilizing peptide of the present invention may comprise peptides having 85% or more (e.g., 85%, 90%, 95%, 97%, 98%, 99%, or 100%) sequence identity to one or more of the sequences listed in Table 1 or any fragments thereof (e.g., fragments of at least 5, 10, 15, or 20 or more consecutive amino acids in length), in particular, the sequences of SEQ ID NOs: 1-12.

TABLE 1

Melittin peptide sequences

| Peptide | Sequence | # acidic residues | # helical spacings | SEQ ID NO: |
|---|---|---|---|---|
| Consensus 1 | GIGX$_1$VLX$_2$X$_3$LAX$_4$X$_5$LPX$_6$LQX$_7$WIX$_8$AAQQL | | | SEQ ID NO: 1 |
| Consensus 2 | GIGX$_1$VLX$_2$X$_3$LAX$_4$X$_5$LPX$_6$LQX$_7$WIX$_8$AAQQL | | | SEQ ID NO: 2 |
| pHD15-30 | GIGEVLHELADDLPDLQEWIHAAQQL | 6 | 9 | SEQ ID NO: 3 |
| pHD24-52 | GIGDVLHELAADLPELQEWIHAAQQL | 5 | 6 | SEQ ID NO: 4 |
| pHD34-20 | GIGEVLKELAADLPELQDWIKAAQQL | 5 | 5 | SEQ ID NO: 5 |
| pHD54-73 | GIGDVLKELADELPALQEWIHAAQQL | 5 | 5 | SEQ ID NO: 6 |
| pHD63-38 | GIGEVLKDLAAELPELQEWIHAAQQL | 5 | 6 | SEQ ID NO: 7 |
| pHD101-77 | GIGEVLKELADELPELQEWIHAAQQL | 6 | 9 | SEQ ID NO: 8 |
| pHD108-47 | GIGEVLHELAEGLPELQEWIHAAQQL | 5 | 6 | SEQ ID NO: 9 |
| pHD118-85 | GIGEVLHELADDLPELQSWIKAAQQL | 5 | 7 | SEQ ID NO: 10 |
| pHD145-40 | GIGDVLKELAEELPLLQEWIKAAQQL | 5 | 5 | SEQ ID NO: 11 |
| pHD187-4 | GIGEVLKDLADLLPELQEWIHAAQQL | 5 | 7 | SEQ ID NO: 12 |
| Melittin | GIGAVLKVLTTGLPALISWIKRKRQQ | 0 | 0 | SEQ ID NO: 13 |
| MelP5 | GIGAVLKVLATGLPALISWIKAAQQL | 0 | 0 | SEQ ID NO: 14 |
| MelP5_Δ4 | GIGAVLKELADGLPALIDWIEAAQQL | 4 | 3 | SEQ ID NO: 15 |
| MelP5_Δ6 | GIGAVLEELADDLPALIDWIEAAQQL | 6 | 5 | SEQ ID NO: 16 |

TABLE 1: Sequences of the natural bee venom pore-former melittin (SEQ ID NO: 13) and its synthetically evolved gain-of-function variant, MelP5 (33), which enables macromolecules to cross bilayers. Using patterns from pH sensitive membrane active peptides, two variants, MelP5_Δ4 and MelP5_Δ6, were previously designed (26). These peptides exhibit pH-triggered membrane activity, but do not induce macromolecular-sized poration (26). Shown are positive peptides that were identified in the screen (depicted by FIG. 3). Peptides are named after the plate and well in which the positive bead was identified. For each peptide, the number of acidic residues, and the number of helical spacings of i to i+3, i to i+4, and i to i+7 between acidic residues are listed.

Based on the sequences of the peptides listed in Table 1, the following consensus sequences were assembled including SEQ ID NO: 1 and SEQ ID NO: 2. Any of SEQ ID NOs: 1-12, and variants thereof, can be used in the compositions and methods described herein.

Consensus Sequence 1

(SEQ ID NO: 1)
GIGX₁VLX₂X₃LAX₄X₅LPX₆LQX₇WIX₈AAQQL

X$_1$ is an acidic amino acid,
X$_2$ is a basic amino acid,
X$_3$ is an acidic amino acid,
X$_4$ is a nonpolar or acidic amino acid,
X$_5$ is a nonpolar or acidic amino acid,
X$_6$ is a nonpolar or acidic amino acid,
X$_7$ is a polar or acidic amino acid, and
X$_8$ is a basic amino acid.

Consensus Sequence 2

(SEQ ID NO: 2)
GIGX₁VLX₂X₃LAX₄X₅LPX₆LQX₇WIX₈AAQQL

X$_1$ is D or E,
X$_2$ is H or K,
X$_3$ is D or E,
X$_4$ is A, D, or E,
X$_5$ is G, L, D, or E,
X$_6$ is A, L, D, or E,
X$_7$ is S, D, or E, and
X$_8$ is H or K.

Functional equivalents of these polypeptides are also intended to be encompassed by this invention. By way of example and not limitation, functionally equivalent polypeptides are those that possess one or more of the following characteristics: the ability to form peptides with little membrane permeabilization at physiological pH 7 at high peptide concentration (e.g., at a P:L ratio of about 1:50 or at a concentration of about 250 µM) or the ability to form peptides with efficient formation of macromolecule-sized defects in membranes at acidic pH 5 and low peptide concentration (e.g., at a P:L ratio of less than about 1:100 (e.g., a P:L ratio of less than about 1:200, about 1:300, about 1:400, about 1:500, about 1:600, about 1:700, about 1:800, or about 1:900) or at a concentration of about 2.5 µM or less).

Also intended to be encompassed are peptidomimetics, which include chemically modified peptides, peptide-like molecules containing non-naturally occurring amino acids, peptoids and the like, and retain the characteristics of the membrane permeabilizing polypeptides provided herein. U.S. Pat. No. 7,144,856 describes compositions that can be employed to produce peptidomimetics, e.g., of the peptides of Table 1 and variants thereof having at least 85% sequence identity thereto.

This invention further includes polypeptides or analogs thereof having substantially the same function as the polypeptides of this invention. Such polypeptides include, but are not limited to, a substitution, addition or deletion mutant of the inventive polypeptides (e.g., in which one, two, three, four, or five amino acids of the polypeptides (e.g., the polypeptides of SEQ ID NOs: 1-16) are substituted with another amino acid or deleted, or in which one, two, three, four, or five amino acids are added to the polypeptides). This invention also encompasses proteins or peptides that are substantially homologous to the polypeptides. A variety of sequence alignment software programs described herein above is available in the art to facilitate determination of homology or equivalence of any protein to a protein of the invention.

In some peptidpes as described herein, D-amino acids may be used instead of or in addition to L-amino acids. Glycine does not have chirality due to two hydrogens. However, all other amino acids may be D-amino acids, including D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL.

Several thousand membrane destabilizing peptides, including antimicrobial peptides and other classes of pore-forming peptides, have been described and investigated over past decades (40-45). Many of these peptides are cationic and destabilize anionic bilayers in a manner driven by strong electrostatic interactions. Efficient permeabilization of zwitterionic phosphatidylcholine (PC) bilayers at low P:L (≤1:100) is uncommon, and efficient release of macromolecules from PC vesicles at low P:L ratios was essentially unknown until the report of the discovery of a novel peptide, MelP5 (32), the disclosure of which is hereby incorporated in its entirety. This peptide is remarkable in its ability to allow the efficient passage of macromolecules through membranes, even at very low peptide-to-lipid ratios (P:L≤1:500 when using 10,000 Da dextran as a probe) where detergent-like vesicle solubilization is unlikely (31, 33). Here, MelP5 was used as a template for an iterative peptide library that was designed and screened to select peptides that cause macromolecular permeabilization of a 40,000 Da dextran at low P:L, like MelP5, but in a pH-dependent manner. The peptides that were identified are remarkably potent, macromolecular-sized pore formers at about pH 5, while having little or no membrane activity at all at about pH 7. All of the selected peptides possess exquisite pH sensitivities, with activities transitioning from ~0 to ~100% over one pH unit, centered on apparent pKa values of 5.5 to 5.8.

All 10 of the positive peptides identified (SEQ ID NOs: 3-12) in the library have 5 or 6 acidic residues out of the 6 possible, despite the fact that only 17% of library members have 5 or 6 acidic residues (see Example 1). The tested peptide with six charges is somewhat less potent and has a lower pKa than the peptides with five charges, as shown in FIG. 4B, suggesting that five negative charges arranged with helical spacing on an amphipathic helix are optimal for the observed pH-triggered activity. The fact that various patterns of 5 acidic residues were observed in the selected positives indicates that the pH sensitivity is due to the physical chemistry of folding and membrane binding. Yet, the specific preference of glutamate compared to aspartate and the 100% conservation of glutamine at position 17 suggests that sequence-specific interaction may also play a role in this activity. In general, toggling the number and position (e.g., around the face of the helix) of acidic residues to alter the pH sensitivity of the peptides.

Figure 6A:
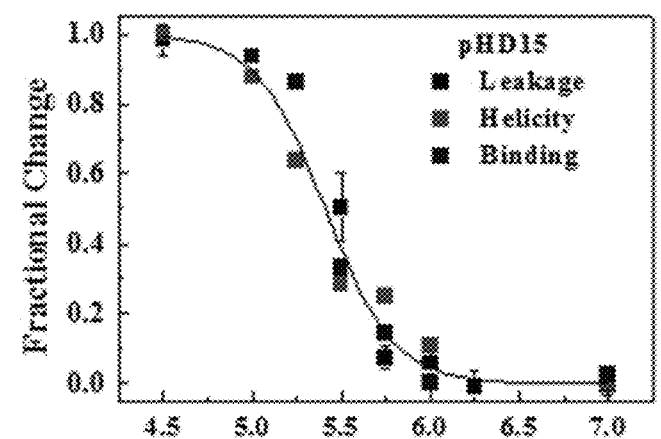
FIGS. 6A-6C are graphs depicting coupling of binding, structure and activity. For three pHD peptides pHD15 (SEQ ID NO: 3.
Figure 6B:
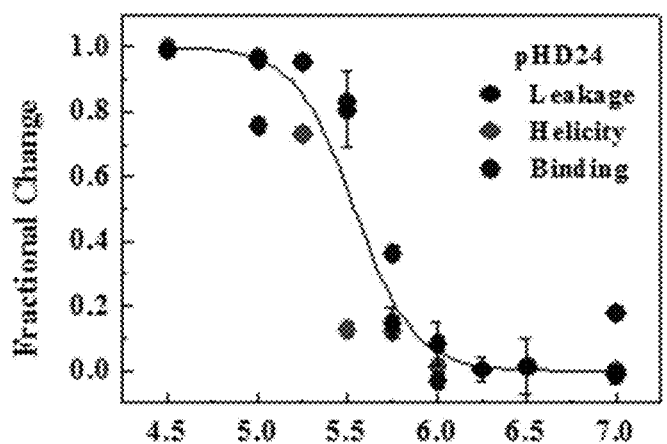
Figure 6C:
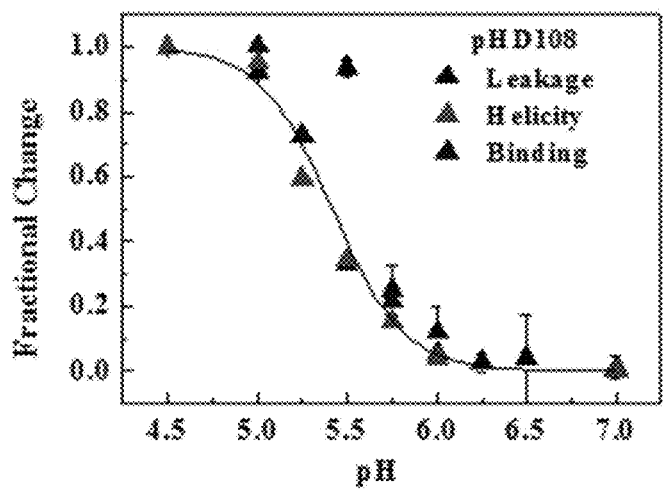
Figure 7A:
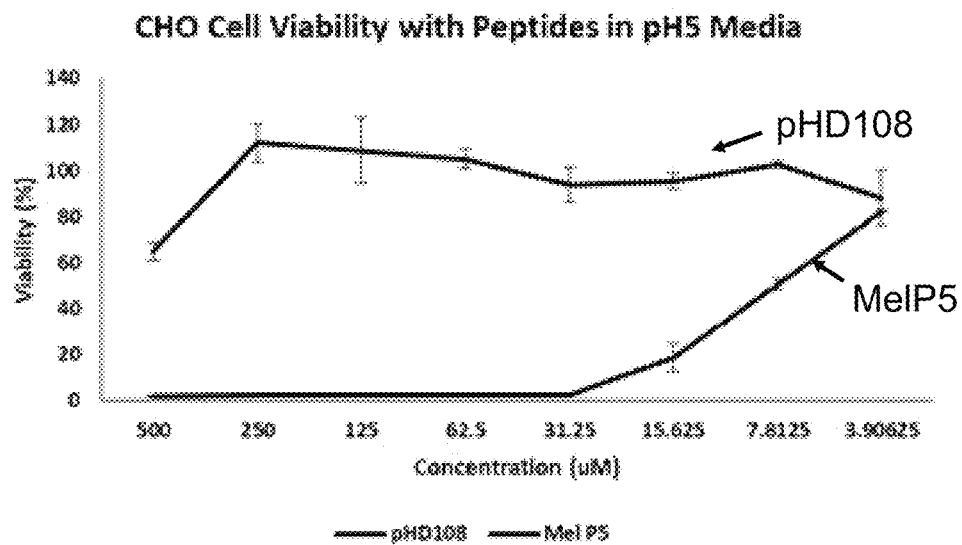
FIGS. 7A-7B are graphs showing the effect of peptides on the viability Chinese Hamster Ovary cells incubated with either the lytic peptide MelP5, or the pH-triggerred membrane permeabilizing peptide pHD108. Cells were grown to 50% confluency, and then treated for ten minutes with peptide in cell culture media at pH 5 (FIG. 7A) or at pH 7 (FIG. 7B). Full media with growth factors was added and the cells recovered overnight. Viability was assessed with the Alamar Blue assay. The values were normalized to cells treated with media only (negative control) and media only, no cells (positive control). The pH-triggered membrane permeabilizing peptide, pHD108, did not exhibit toxicity to mammalian cells at either pH tested except at the highest concentration.
Figure 7B:
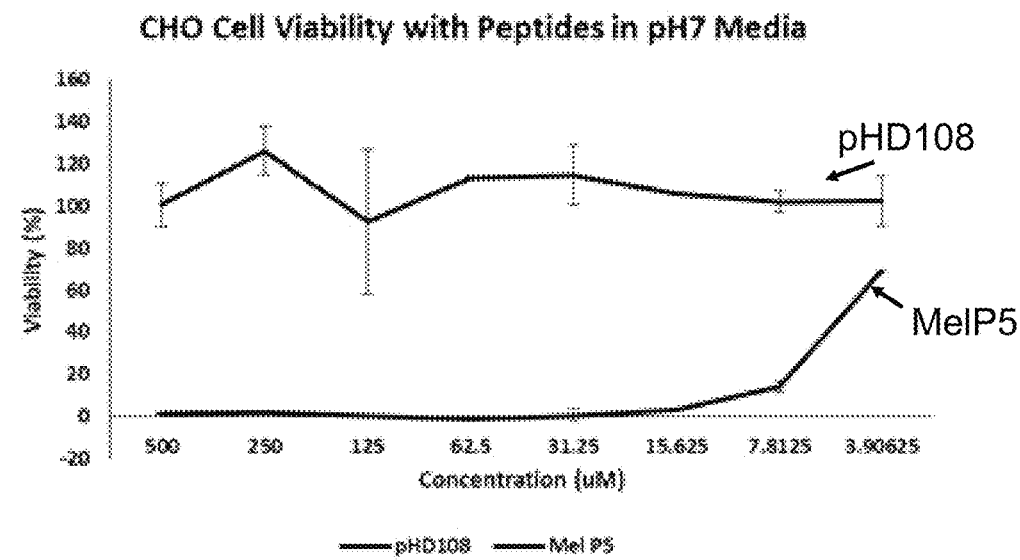

According to the Henderson-Hasselbalch equation, an equilibrium that simply reflects protonation of glutamate or aspartate should transition from 10% to 90% complete over two pH units. However, transitions were observed in dextran leakage, secondary structure, and binding by the peptides of interest here, termed pH-triggered destroyer (pHD) peptides, from near 0% to near 100% over one pH unit, as shown in FIGS. 6A-6C, indicative of highly cooperative behavior. Furthermore, the apparent pKa values that were measured for the selected peptides range from 5.5 to 5.8, much higher than the pKa of ~3.5 to ~4.0 expected for the free side chains for Glu or Asp. It is hypothesized that the tight coupling between membrane partitioning, α-helix formation, and electrostatic repulsion between acidic sidechains drives both the upward shift in pKa, relative to that of the free sidechains, and the unexpectedly sharp transition. Potentially favorable electrostatic interactions between the basic lysine and histidine residues and some of the acidic sidechains may also contribute to the pH sensitivity.

Figure 5A:
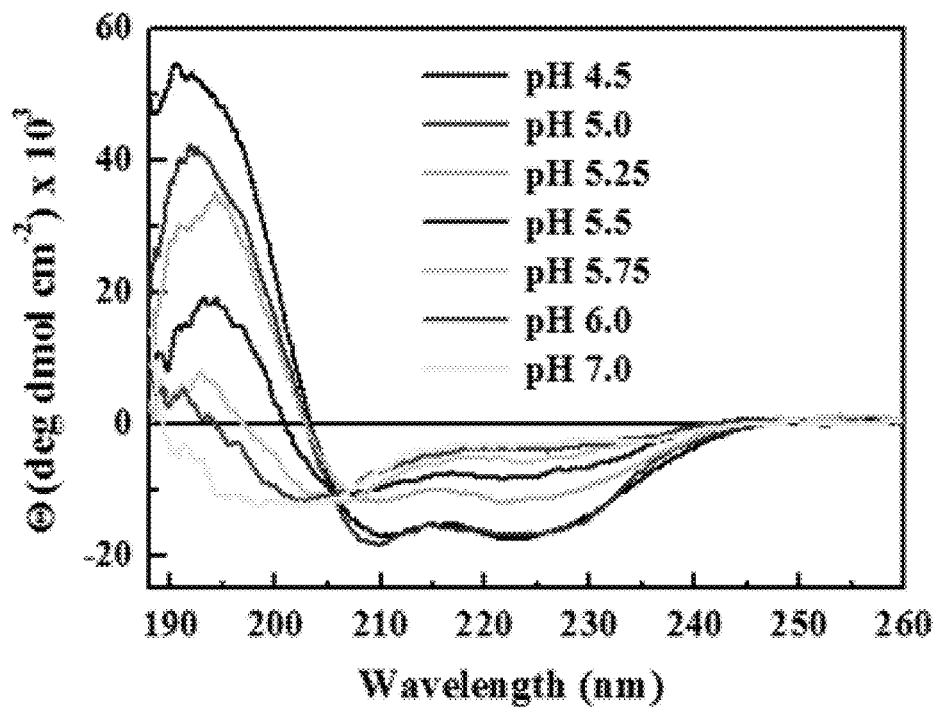
FIGS. 5A-5B are graphs depicting example binding and folding data.

To estimate the protonation state of the peptide, Membrane Protein Explorer (MPEx) (46) was used to predict free energies of membrane partitioning of the pHD peptides compared to MelP5. Assuming that bound peptides are 75% α-helix, as shown in FIG. 5A (32), protonation of at least 4 or 5 of the acidic sidechains in the pHD peptides would be required for the strong membrane partitioning that was observed at pH 5. Thus, it was hypothesized that most of the acidic sidechains in the pHD peptides are cooperatively protonated with an apparent pKa of ~5.5-~5.8.

Previous work attempted to engineer pH sensitivity into the unique macromolecular poration activity of MelP5 but failed. Here the goal of pH-triggered macromolecular poration was achieved using a fundamentally different approach: synthetic molecular evolution, which is accomplished with orthogonal screening of a rationally designed, iterative, combinatorial peptide library. The data disclosed herein demonstrates that synthetic molecular evolution is a powerful method to drive the discovery of pore-forming peptides with specific membrane activities.

The selected peptides cause pH-triggered macromolecular poration, a property that may be exploited in multiple ways. There are many applications in medicine where acidic environmental pH could be used to trigger the activity of the new peptides. One example is in the acidic environment around solid tumors (12), where tumor selective cytolytic activity may be triggered. A second example is acidified organelles, such as endosomes and lysosomes (16, 47-49), where selective cargo delivery into the cytosol could be enabled by pH-induced macromolecular poration.

Polynucleotides

The invention also features polynucleotides that encode the polypeptides described herein (e.g., peptides having 85% identity to one or more of the peptides listed in Table 1 (e.g., peptides of SEQ ID NOs: 1-12)). The term polynucleotide is used broadly and refers to polymeric nucleotides of any length (e.g., oligonucleotides, genes, small inhibiting RNA, fragments of polynucleotides encoding a protein, etc). By way of example and not limitation, the polynucleotides of the invention may comprise a sequence encoding all or part of a membrane permeabilizing peptide (e.g., the peptides of Table 1 and peptides having at least 85% sequence identity thereto). The polynucleotide of the invention may be, for example, linear, circular, supercoiled, single-stranded, double-stranded, branched, partially double-stranded or partially single-stranded. The nucleotides comprised within the polynucleotide may be naturally occurring nucleotides or modified nucleotides.

Functional equivalents of these polynucleotides are also intended to be encompassed by this invention. By way of example and not limitation, functionally equivalent polynucleotides are those that encode peptides that possess one or more of the following characteristics: the ability to form peptides with little membrane permeabilization at physiological pH 7 at high peptide concentration or the ability to form peptides with efficient formation of macromolecule-sized defects in membranes at acidic pH 5 and low peptide concentration.

Polynucleotide sequences that are functionally equivalent may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. Other similar analysis and alignment programs can be purchased from various providers, such as DNA Star's MegAlign, or the alignment programs in GeneJockey. Alternatively, sequence analysis and alignment programs can be accessed through the world wide web at sites such as the CMS Molecular Biology Resource at sdsc.edufResTools/cmshp.html. and ExPASy Proteomics Server at www.expasy.ch/. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al., *Proc. Natl. Acad. Sci.* (*USA*) 87: 2246, 1990. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

Expression Vectors

Also featured are expression vectors comprising at least one polynucleotide encoding a peptide of the invention or fragment thereof (e.g., a fragment that retains the ability to form pH-sensitive macromolecular pore-formation). For example, an expression vector includes a polynucleotide encoding one or more of the peptides of Table 1 and variants thereof having 85% sequence identity thereto. Expression vectors are well known in the art and include, but are not limited to viral vectors or plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), adenovirus vectors, alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system and herpes virus.

Nonviral vectors, such as plasmids, are also well known in the art and include, but are not limited to, yeast- and bacteria-based plasmids. Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells, such as NS0 and CHO cells.

By way of example, vectors comprising the polynucleotide of the invention may further comprise a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further comprise a polynucleotide sequence encoding a linker sequence. Generally the linking sequence is positioned in the vector between the membrane permeabilizing peptide-encoding polynucleotide sequence and the polynucleotide tag sequence. Linking sequences can encode random amino acids or can contain functional sites. Examples of linking sequences containing functional sites include but are not limited to, sequences containing the Factor Xa cleavage site, the thrombin cleavage site, or the enterokinase cleavage site.

By way of example, and not limitation, a membrane permeabilizing peptide may be generated as described herein using mammalian expression vectors in mammalian cell culture systems or bacterial expression vectors in bacterial culture systems. Primers may be used to amplify the desired sequence from a template.

Lipid Vesicles

The invention also features lipid bilayers and lipid vesicles containing the pore forming peptides embedded therein. The peptides described herein may be incorporated into lipid bilayers and/or lipid vesicles. Lipid bilayers (e.g., phospholipid bilayers) are polar membranes made of two layers of lipid molecules. Exemplary lipids are laurate, myristate, palmitate, oleate, cholesterol, and PEG-cholesterol. The polar head groups are hydrophilic while the lipid tails are hydrophobic. The peptides described herein may be amphiphilic such that they have both hydrophobic and hydrophilic properties to allow them to reside within and interact with the phospholipids within a lipid bilayer. Lipid bilayers may form (e.g., spontaneously) lipid vesicles based on the critical micelle concentration (CMC) of the lipids. Lipid vesicles are polar vesicles with an aqueous core. The size of the lipid vesicles and the CMC may be modulated by using lipids with different sized and charged head groups and tails.

Lipid vesicles may be used to store cargo (e.g., a therapeutic agent, diagnostic agent, and an antigen (e.g., for use as a vaccine)) that can be targeted and/or delivered to a specific site (e.g., a cancer cell). Any cargo may be stored within the lipid vesicle (e.g., in the aqueous core of the lipid vesicle or in the lipid bilayer). The size of the lipid vesicles may be optimized to store different types and sizes of cargo. Vesicles can be assembled, for example, by dialyzing a cargo with phospholipids and detergent and slowly removing the detergent until the phospholipid concentration drops below the CMC and assembles into a vesicle. Other components may also be added into the assembly mixture, such as pore-forming peptides or other moieties (e.g., targeting agents, antibodies, chimeric antigen receptors, tumor associated antigens) that may be embedded into or decorate the lipid bilayer. Targeting agents on the lipid vesicle may allow the vesicle to be directed to a specific cell type (e.g., a cancer cell) or cellular location (e.g., a tumor site).

Methods of Treatment

Generally, a composition comprising a lipid vesicle coated with a targeting agent and loaded with a therapeutic agent (e.g., a cancer therapeutic agent) can be administered (e.g., intravenously) to a subject (e.g., a cancer patient) as a medicament (e.g., for treating cancer). The targeting agent confers the vesicle specificity such that it directs the therapeutic agent to the appropriate cell type or cell compartment where treatment is desired. For example, a tumor associated antigen (TAA) may be expressed on a cancer cell surface. Thus, an antibody on the surface of the vesicle (e.g., linked to a lipid) that is specific for that TAA would direct the vesicle to the cancer cell. Once the lower pH around the target cancer cell triggers the macromolecular assembly of the pore-forming peptides, a therapeutic agent that is stored as cargo within the lipid vesicle may be specifically delivered to the cancer cell, thus killing the cell.

Targeting to specific cell types in vivo may also be accomplished with receptor ligands. For example, the vesicles may be directed to the uptake pathways in the certain cell types using these ligands. For example, the lipid vesicle may be endocytosed by a target cell. Upon endocytosis, a change in pH (e.g., due to the acidity of organelles, such as endosomes and lysosomes) triggers pore-formation within the membrane of the vesicle and the therapeutic cargo contents are released inside the targeted organelle (e.g., lysosome, endosome, and nucleus) and/or cell (see also Example 11).

Vaccines

The cargo within lipid vesicles may include vaccines, such as vaccines for cancer and other diseases (e.g., vaccines containing one or more cancer antigens). In one aspect the vaccines are DNA-based vaccines. One skilled in the art is familiar with administration of expression vectors to obtain expression of an exogenous protein in vivo. See, e.g., U.S. Pat. Nos. 6,436,908; 6,413,942; and 6,376,471, incorporated herein by reference. Viral-based vectors for delivery of a desired polynucleotide and expression in a desired cell are well known in the art and non-limiting examples are described herein.

Routes of administration of compositions for use as a vaccine include local and systemic administration, including injection, oral administration, particle gun or catheterized administration, and topical administration. Therapeutic compositions (e.g., vaccine compositions, such as a DNA-based expression vector or subgenomic polynucleotides) can also modidified to achieve targeted delivery (e.g., using antibodies, receptors, or receptor ligands). For example, receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Non-viral delivery vehicles and methods can also be employed, including but not limited to, polycationic condensed DNA linked or unlinked to killed adenovirus alone (see, e.g., Cunel, *Hum. Gene Ther.* (1992) 3:147); ligand-linked DNA (see, e.g., Wu, *J. Biol. Chem.* (1989) 264: 16985); eukaryotic cell delivery vehicles (see, e.g., U.S. Pat. No. 5,814,482; PCT Publication Nos. WO 95/07994; WO 96/17072; WO 95/30763; and WO 97/42338); and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796, WO 94/23697, WO 91/14445; and EP 0524968. Additional approaches are described in Philip, *Mol. Cell Biol.* (1994) 14:2411, and in Woffendin, *Proc. Natl. Acad. Sci.* (1994) 91:1581.

For human administration, the codons comprising the polynucleotide encoding one or more membrane permeabilizing peptides may be optimized for human use, a process that is standard in the art.

In another aspect of the invention, one or more membrane permeabilizing peptides or pore-forming fragments or combinations thereof can be used as a vaccine. The one or more peptides, fragments, or combinations thereof may be administered by alone or in combination with an adjuvant. Examples of adjuvants include, but are not limited to, aluminum salts, water-in-oil emulsions, oil-in-water emulsions, saponin, QuilA and derivatives, iscoms, liposomes, cytokines including gamma-interferon or interleukin 12, DNA (e.g. unmethylated poly-CpG), microencapsulation in a solid or semi-solid particle, Freunds complete and incomplete adjuvant or active ingredients thereof including muramyl dipeptide and analogues, DEAE dextrarilmineral oil, Alhydrogel, Auspharm adjuvant, and Algammulin.

The vaccine comprising one or more membrane permeabilizing peptides or pore-forming fragments or combinations thereof can be administered orally or by any parenteral route such as intravenously, subcutaneously, intraarterially, intramuscularly, intracardially, intraspinally, intrathoracically, intraperitoneally, intraventricularly, sublingually, and/or transdermally.

Dosage and schedule of administration can be determined by methods known in the art. Efficacy of the one or more membrane permeabilizing peptides or fragments or combinations thereof as a vaccine for cancer or other diseases may also be evaluated by methods known in the art.

Cancer

The compositions and methods described herein may be used to treat cancer. For example, a lipid vesicle carrying a cargo (e.g., a cancer therapeutic agent) can be targeted to a particular cancer cell through a targeting molecule (e.g., an antibody, receptor, receptor binding ligand, TAA, or a combination thereof). Once the vesicle comes into contact with target cell (e.g., a cancer cell), the pore forming peptide can be induced (e.g., via a pH change) to porate the target cell (e.g., a cancer cell) and deliver the cargo through the pore or to deliver the cargo at a site near the target cell (e.g., in an acidic environment near the target cell).

Exemplary cancers that may be treated by the invention as described herein include such cancers as leukemia, lymphoma, liver cancer, bone cancer, lung cancer, brain cancer, bladder cancer, gastrointestinal cancer, breast cancer, cardiac cancer, cervical cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, hodgkin lymphoma, hypopharyngeal cancer, islet cell tumors, pancreatic neuroendocrine tumors, wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, pheochromocytoma, pituitary tumor, pleuropulmonary blastoma, primary peritoneal cancer, rectal cancer, retinoblastoma, rhabdomyosarcoma, salivary gland cancer, kaposi sarcoma, rhabdomyosarcoma, sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, and Waldenström macroglobulinemia.

Chemotherapeutic agents that may be used in conjunction with the compositions and methods as described herein include, without limitation, Abiraterone Acetate, ABITREXATE® (Methotrexate), ABRAXANE® (Paclitaxel Albumin), ADCETRIS® (Brentuximab Vedotin), ado-trastuzumab emtansine, ADRIAMYCIN® (doxorubicin hydrochloride), afatinib dimaleate, AFINITOR® (Everolimus), AKYNZEO® (netupitant and palonosetron hydrochloride), ALDARA® (imiquimod), aldesleukin, ALECENSA® (alectinib), alectinib, alemtuzumab, ALKERAN® for Injection (Melphalan Hydrochloride), ALKERAN® tablets (melphalan), ALIMTA® (pemetrexed disodium), ALOXI® (palonosetron hydrochloride), AMBOCHLORIN® (chlorambucil), AMBOCLORIN® (Chlorambucil), aminolevulinic acid, anastrozole, aprepitant, AREDIA® (pamidronate disodium), ARIMIDEX® (anastrozole), AROMASIN® (exemestane), ARRANON® (nelarabine), arsenic trioxide, ARZERRA® (ofatumumab), asparaginase *Erwinia chrysanthemi*, AVASTIN® (bevacizumab), axitinib, azacitidine, BELEODAQ® (Belinostat), belinostat, bendamustine hydrochloride, bevacizumab, bexarotene, BEXXAR® (tositumomab and iodine $^{131}$I tositumomab), bicalutamide, BiCNU (carmustine), bleomycin, blinatumomab, BLINCYTO® (blinatumomab), bortezomib, BOSULIF® (bosutinib), bosutinib, brentuximab vedotin, busulfan, BUSULFEX® (busulfan), cabazitaxel, cabozantinib-S-malate, CAMPATH® (alemtuzumab), CAMPTOSAR® (irinotecan hydrochloride), capecitabine, CAPDX, CARAC® (fluorouracil), carboplatin, CARBOPLATIN-TAXOL®, carfilzomib, CARMUBRIS® (carmustine), carmustine, carmustine implant, CASODEX® (bicalutamide), CEENU (lomustine), ceritinib, CERUBIDINE® (daunorubicin hydrochloride), CERVARIX® (recombinant HPV bivalent vaccine), cetuximab, chlorambucil, chlorambucil-prednisone, cisplatin, CLAFEN® (cyclophosphamide), clofarabine, CLOFAREX® (clofarabine), CLOLAR® (Clofarabine), cobimetinib, cometriq (cabozantinib-S-malate), COSMEGEN® (dactinomycin), COTELLIC® (cobimetinib), crizotinib, CVP, cyclophosphamide, CYFOS® (ifosfamide), CYRAMZA® (ramucirumab), cytarabine, cytarabine liposome, CYTOSAR-U® (cytarabine), CYTOXAN® (cyclophosphamide), dabrafenib, dacarbazine, DACOGEN® (decitabine), dactinomycin, daratumumab, DARZALEX® (daratumumab), dasatinib, daunorubicin hydrochloride, decitabine, degarelix, denileukin diftitox, denosumab, DEPOCYT® (cytarabine liposome), dexamethasone, dexrazoxane hydrochloride, dinutuximab, docetaxel, DOXIL® (doxorubicin hydrochloride), doxorubicin hydrochloride, DOX-SL® (doxorubicin hydrochloride), DTIC-DOME® (dacarbazine), EFUDEX (fluorouracil), ELITEK® (rasburicase), ELLENCE® (epirubicin hydrochloride), elotuzumab, ELOXATIN® (oxaliplatin), eltrombopag olamine, EMEND® (aprepitant), EMPLICITI® (elotuzumab), enzalutamide, epirubicin hydrochloride, ERBITUX® (cetuximab), eribulin mesylate, ERIVEDGE® (vismodegib), erlotinib hydrochloride, ERWINAZE (asparaginase *Erwinia chrysanthemi*), ETOPOPHOS® (etoposide phosphate), etoposide, etoposide phosphate, EVACET® (doxorubicin hydrochloride liposome), everolimus, EVISTA® (raloxifene hydrochloride), EVOMELA® (melphalan hydrochloride), exemestane, 5-FU (5-fluorouracil), FARESTON® (toremifene), FARYDAK® (panobinostat), FASLODEX® (fulvestrant), FEMARA® (letrozole), filgrastim, FLUDARA® (fludarabine phosphate), fludarabine phosphate, FLUOROPLEX® (fluorouracil), fluorouracil injection, flutamide, FOLEX® (methotrexate), FOLEX® PFS (methotrexate), fulvestrant, GARDASIL® (recombinant HPV quadrivalent vaccine), GARDASIL 9® (recombinant HPV nonavalent vaccine), GAZYVA® (obinutuzumab), gefitinib, gemcitabine hydrochloride, gemcitabine-cisplatin, gemcitabine-oxaliplatin, gemtuzumab ozogamicin, GEMZAR® (gemcitabine hydrochloride), GILOTRIF® (afatinib dimaleate), GLEEVEC® (imatinib mesylate), GLIADEL® (carmustine implant), GLIADEL® wafer (carmustine implant), glucarpidase, goserelin acetate, HALAVEN® (eribulin mesylate), HERCEPTIN® (trastuzumab), HPV bivalent vaccine, HYCAMTIN® (topotecan hydrochloride), IBRANCE (palbociclib), IBRITUMOMAB® tiuxetan, ibrutinib, ICLUSIG® (ponatinib hydrochloride), IDAMYCIN® (idarubicin hydrochloride), idarubicin hydrochloride, idelalisib, IFEX® (ifosfamide), ifosfamide, ifosfamidum, IL-2 (aldesleukin), imatinib mesylate, IMBRUVICA® (ibrutinib), ilmiquimod, IMLYGIC® (talimogene laherparepvec), INLYTA (axitinib), recombinant interferon alpha-2b, intron A, tositumomab, such as $^{131}$I tositumomab, ipilimumab, IRESSA® (gefitinib), irinotecan hydrochloride, ISTODAX® (romidepsin), ixabepilone, ixazomib citrate, IXEMPRA® (ixabepilone), JAKAFI® (ruxolitinib phosphate), JEVTANA® (cabazitaxel), KADCYLA® (ado-trastuzumab emtansine), KEOXIFENE® (raloxifene hydrochloride), KEPIVANCE® (palifermin), KEYTRUDA® (pembrolizumab), KYPROLIS® (carfilzomib), lanreotide acetate, lapatinib ditosylate, lenalidomide, lenvatinib mesylate, LENVIMA® (lenvatinib mesylate), letrozole, leucovorin calcium, leukeran (chlorambucil), leuprolide acetate, levulan (aminolevulinic acid), LINFOLIZIN® (chlorambucil), LIPODOX® (doxorubicin hydrochloride liposome), lomustine, LONSURF® (trifluridine and tipiracil hydrochloride), LUPRON® (leuprolide acetate), LYNPARZA® (olaparib), MARQIBO® (vincristine sulfate liposome), MATULANE® (procarbazine hydrochloride), mechlorethamine hydrochloride, megestrol acetate, MEKINIST® (trametinib), melphalan, melphalan hydrochloride, mercaptopurine, MESNEX® (mesna), METHAZOLASTONE® (temozolomide), methotrexate, methotrexate LPF, MEXATE® (methotrexate), MEXATE-AQ® (methotrexate), mitomycin C, mitoxantrone hydrochloride, MITOZYTREX® (mitomycin C), MOZOBIL® (plerixafor), MUSTARGEN® (mechlorethamine hydrochloride), MUTAMYCIN® (mitomycin C), MYLERAN® (busulfan), MYLOSAR® (azacitidine), MYLOTARG® (gemtuzumab ozogamicin), nanoparticle paclitaxel, NAVELBINE® (vinorelbine tartrate), NECITUMUMAB, nelarabine, NEOSAR® (cyclophosphamide), netupitant and palonosetron hydrochloride, NEUPOGEN® (filgrastim), NEXAVAR® (sorafenib tosylate), NILOTINIB, NINLARO® (ixazomib citrate), nivolumab, NOLVADEX® (tamoxifen citrate), NPLATE® (romiplostim), obinutuzumab, ODOMZO® (sonidegib), ofatumumab, olaparib, omacetaxine mepesuccinate, ONCASPAR® (pegaspargase), ondansetron hydrochloride, ONIVYDE® (irinotecan hydrochloride liposome), ONTAK® (denileukin diftitox), OPDIVO® (nivolumab), osimertinib, oxaliplatin, paclitaxel, paclitaxel albumin-stabilized nanoparticle formulation, palbociclib, palifermin, palonosetron hydrochloride, palonosetron hydrochloride and netupitant, pamidronate disodium, panitumumab, panobinostat, PARAPLAT® (carboplatin), PARPLATIN® (carboplatin), pazopanib hydrochloride, pegaspargase, peginterferon alpha-2b, PEG-INTRON® (peginterferon alpha-2b), pembrolizumab, pemetrexed disodium, PERJETA® (pertuzumab), pertuzumab, PLATINOL® (cisplatin), PLATINOL-AQ® (cisplatin), plerixafor, pomalidomide, POMALYST® (pomalidomide), ponatinib hydrochloride, PORTRAZZA® (necitumumab), pralatrexate, prednisone, procarbazine hydrochloride, PROLEUKIN® (aldesleukin), PROLIA® (denosumab), PROMACTA (eltrombopag olamine), PROVENGE® (sipuleucel-T), PURINETHOL® (mercaptopurine), PURIXAN® (mercaptopurine), $^{223}$Ra dichloride, raloxifene hydrochloride, ramucirumab, rasburicase, recombinant human papillomavirus (HPV), recombinant interferon alpha-2b, regorafenib, REVLIMID® (lenalidomide), RHEUMATREX® (methotrexate), RITUXAN® (rituximab), rolapitant hydrochloride, romidepsin, romiplostim, rubidomycin (daunorubicin hydrochloride), ruxolitinib phosphate, SCLEROSOL® intrapleural aerosol (talc), siltuximab, sipuleucel-T, somatuline depot (lanreotide acetate), sonidegib, sorafenib tosylate, SPRYCEL® (dasatinib), sterile talc powder (talc), STERITALC® (talc), STIVARGA® (regorafenib), sunitinib malate, SUTENT® (sunitinib malate), SYLATRON® (peginterferon alpha-2b), SYLVANT® (siltuximab), SYNOVIR® (thalidomide), SYNRIBO® (omacetaxine mepesuccinate), thioguanine, TAFINLAR® (dabrafenib), TAGRISSO® (osimertinib), talimogene laherparepvec, tamoxifen citrate, tarabine PFS (cytarabine), TARCEVA (erlotinib hydrochloride), TARGRETIN® (bexarotene), TASIGNA® (nilotinib), TAXOL® (paclitaxel), TAXOTERE® (docetaxel), TEMODAR® (temozolomide), temsirolimus, thalidomide, THALOMID® (thalidomide), thioguanine, thiotepa, TOLAK® (topical fluorouracil), topotecan hydrochloride, toremifene, TORISEL® (temsirolimus), TOTECT® (dexrazoxane hydrochloride), trabectedin, trametinib, TREANDA® (bendamustine hydrochloride), trifluridine and tipiracil hydrochloride, TRISENOX® (arsenic trioxide), TYKERB® (lapatinib ditosylate), UNITUXIN® (dinutuximab), uridine triacetate, vandetanib, VARUBI® (rolapitant hydrochloride), vectibix (panitumumab), VELBAN® (vinblastine sulfate), VELCADE® (bortezomib), VELSAR (vinblastine sulfate), VEMURAFENIB, VIADUR (leuprolide acetate), VIDAZA (azacitidine), vinblastine sulfate, VINCASAR® PFS (vincristine sulfate), vincristine sulfate, vinorelbine tartrate, vismodegib, VISTOGARD® (uridine triacetate), VORAXAZE® (glucarpidase), vorinostat, VOTRIENT® (pazopanib hydrochloride), WELLCOVORIN® (leucovorin calcium), XALKORI® (crizotinib), XELODA® (capecitabine), XGEVA® (denosumab), XOFIGO® ($^{223}$Ra dichloride), XTANDI® (enzalutamide), YERVOY® (ipilimumab), YONDELIS® (trabectedin), ZALTRAP® (ziv-aflibercept), ZARXIO® (filgrastim), ZELBORAF® (vemurafenib), ZEVALIN® (ibritumomab tiuxetan), ZINECARD® (dexrazoxane hydrochloride), ziv-aflibercept, ZOFRAN® (ondansetron hydrochloride), ZOLADEX® (gGoserelin acetate), zoledronic acid, ZOLINZA® (vorinostat), ZOMETA® (zoledronic acid), ZYDELIG® (idelalisib), ZYKADIA® (ceritinib), and ZYTIGA (abiraterone acetate), or is selected from the following combinations of agents: ADRIAMYCIN®, bleomycin, vinblastine, and dacarbazine (ABVD); ADRIAMYCIN®, bleomycin, vincristine sulfate, and etoposide phosphate (ABVE); ADRIAMYCIN®, bleomycin, vincristine sulfate, etoposide phosphate, prednisone, and cyclophosphamide (ABVE-PC); doxorubicin and cyclophosphamide (AC); doxorubicin, cyclophosphamide, and paclitaxel or docetaxel (ACT); cytarabine (Ara-C), daunorubicin, and etoposide (ADE); cyclophosphamide, doxorubicin hydrochloride, vincristine sulfate, and prednisone (CHOP); etoposide phosphate, prednisone, vincristine sulfate (Oncovin), cyclophosphamide, and doxorubicin hydrochloride (hydroxydaunorubicin) (EPOCH); rituximab, etoposide phosphate, prednisone, vincristine sulfate (oncovin), cyclophosphamide, and doxorubicin hydrochloride (hydroxydaunorubicin) (R-EPOCH); folinic acid, fluorouracil, and irinotecan (FOLIFIRI); FOLFIRI-bevacizumab; FOLFIRI-cetuximab; folinic acid, fluorouracil, irinotecan, and oxaliplatin (FOLIFIRINOX); folinic acid, flurouracil, and oxaliplatin (FOLFOX); FOLOTYN® (pralatrexate), fluorouracil and leucovorin (FU-LV); rituximab, ifosamide, carboplatin, etoposide (ICE); rituximab, cyclophosphamide, doxorubicin hydrochloride, vincristine sulfate, and prednisone (R-CHOP); irinotecan and capecitabine (XELIRI); oxaliplatin and capecitabine (XELOX); bleomycin, etoposide, Adriamycin, cyclophosphamide, oncovin, procarbazine, prednisone (BEACOPP); bleomycin, etoposide, and cisplatin (BEP); cyclophosphamide, doxorubicin, and 5-Fluorouracil (CAF); capecitabine and oxaliplatin (CAPDX); cisplatin, etoposide, and methotrexate (CEM); cyclophosphamide, methotrexate, and fluorouracil (CMF); cyclophosphamide, oncovin, prednisone, and dacarbazine (COPDAC); cyclophosphamide, oncovin, procarbazine hydrochloride, and prednisone (COPP); COPP, Adriamycin, bleomycin, and vinblastine sulfate (COPP-ABV); cyclophosphamide, vincristine, and prednisolone (CVP); 5'-fluorouracil, epirubicin, cyclophosphamide (FEC); hyper cyclophosphamide, vincristine, adriamycin (hyper-CVAD); mutargen, oncovin, procarbazine, and prednisone (MOPP); oncovin, etoposide phosphate, prednisone, and Adriamycin (OEPA); oxaliplatin, fluorouracil, and leucovorin (OFF); oncovin, prednisone, procarbazine hydrochloride, and Adriamycin (OPPA); bortezomib, dexamethasone, and doxorubicin (PAD); procarbazine, lomustine, and vincristine (PCV); rituximab, cyclophosphamide, vincristine sulfate, and prednisone (R-CVP); doxorubicin, vinblastine, mechlorethamine, vincristine, bleomycin, etoposide, and prednisone (STANFORD V); docetaxel, Adriamycin, and cyclophosphamide (TAC); taxotere, platinol, and fluorouracil (TPF); vincristine sulfate, actinomycin-D, and cyclophosphamide (VAC); vincristine, amethopterine, methotrexate, and prednisone (VAMP); vincristine sulfate, etoposide, L-asparaginase, and prednisone acetate (VELP); and vepesid, ifosfamide, and platinol (VIP).

A lipid vesicle may target a cancer cell by way of a targeting molecule that binds to the cancer cell. In some instances, the cancer cell will express an antigen on its surface that can be used for targeting, e.g., with an antibody. A target may be a cancer antigen or tumor-associated antigen. Tumor-associated antigens (TAAs) include protein antigens that are overexpressed on the surface of a cancer cell relative to a non-cancerous cell, as well as proteins that arise from mutations of wild-type proteins. A TAA may be tumor-specific, in which case the expression of the antigen is restricted to a particular type of cancer cell. Alternatively, a TAA may be common to several cancers and thus expressed on the surface of a variety of cancer cell types. Examples of TAAs that can be expressed by or conjugated to a lipid vesicle described herein include one or more tumor-associated antigens listed in the Table 2. For example, the TAA may be an ovarian cancer TAA, a breast cancer TAA, a testicular cancer TAA, a pancreatic cancer TAA, a liver cancer TAA, a colorectal cancer TAA, a thyroid cancer TAA, a lung cancer TAA, a prostate cancer TAA, a kidney cancer TAA, a melanoma TAA, a squamous cell carcinoma TAA, a chronic myeloid leukemia TAA, an acute lympoblastic leukemia TAA, an acute myelogenous leukemia TAA, a chronic lympocytic leukemia TAA, a promyelocytic leukemia TAA, a multiple myeloma TAA, a B cell lymphoma TAA, a bladder carcinoma TAA, a head and neck cancer TAA, an esophageal cancer TAA, a brain cancer TAA, a pharynx cancer TAA, a tumor of the tongue TAA, a synovial cell sarcoma TAA, a neuroblastoma TAA, or a uterine cancer TAA, non-limiting examples for each of which are further listed in the Appendix. Additional examples of TAAs are known in the art and are described, e.g., in Reuschenbach et al., *Cancer Immunol. Immunother.* 58:1535-1544 (2009); Parmiani et al., J. Nat. Cancer Inst. 94:805-818 (2002); Zarour et al., *Cancer Medicine.* (2003); Bright et al., *Hum. Vaccin. Immunother.* 10:3297-3305 (2014); Wurz et al., *Ther. Adv. Med. Oncol.* 8:4-31 (2016); Criscitiello, *Breast Care* 7:262-266 (2012); Chester et al., *J. Immunother. Cancer* 3:7 (2015); Li et al., *Mol. Med. Report* 1:589-594 (2008); Liu et al., *J. Hematol. Oncol.* 3:7 (2010); Bertino et al., *Biomed. Res. Int.* 731469 (2015); and Suri et al., *World J. Gastrointest. Oncol.* 7:492-502 (2015), the disclosures of each of which are incorporated herein by reference in their entirety.

Exemplary TAAs are listed in Table 2. Any molecule (e.g. an antibody) that binds to the TAA or any epitope within the TAA may be used to target a vesicle to the cancer.

TABLE 2

| Cancer type and TAAs | |
|---|---|
| Cancer type | Tumor associated antigen (TAA) |
| Ovarian cancer | Kallikrein 4, PBF, PRAME, WT1, HSDL1, Mesothelin, NY-ESO-1, CEA, p53, Her2/Neu, EpCAM, CA125, Folate receptor α, Sperm protein 17, TADG-12, MUC-16, L1CAM, Mannan-MUC-1, HERV-K-MEL, KK-LC-1, KM-HN-1, LAGE-1, MAGE-A4, Sp17, SSX-4, TAG-1, TAG-2 |
| Breast cancer | ENAH (hMena), mammaglobin-A, NY-BR-1, EpCAM, NY-ESO-1, BAGE-1, HERV-K-MEL, KK-LC-1, KM-HN-1, LAGE-1, MAGE-A1, MAGE-A2, mucink, Sp17, SSX-2, TAG-1, TAG-2, TRAG-3, Her2/Neu, c-myc, cyclin B1, MUC1, p53, p62, Survivin |
| Testicular cancer | CD45, DKK1, PRAME, RU2AS, Telomerase |
| Pancreatic cancer | ENAH (hMena), PBF, K-ras, Mesothelin, mucink |
| Liver cancer | G250/MN/CAIX, Hepsin, Intestinal carboxyl esterase, alpha-foetoprotein, M-CSF, PBF, PSMA NY-ESO-1, LAGE-1, HERV-K-MEL, KK-LC-1, KM-HN-1, Sp17, c-myc, cyclin B1, p53, p62, Survivin |
| Colorectal cancer | ENAH (hMena), Intestinal carboxyl esterase, CASP-5, COA-1, OGT, OS-9, TGF-betaRII, NY-ESO-1, CEA, HERV-K-MEL, KK-LC-1, KM-HN-1, LAGE-1, MAGE-A2, Sp17, TAG-1, TAG-2, c-myc, cyclin B1, MUC1, p53, p62, Survivin, gp70 |
| Thyroid cancer | CALCA, NY-ESO-1, HERV-K-MEL, KK-LC-1, KM-HN-1, LAGE-1, Sp17 |
| Lung cancer | CD274, mdm-2, alpha-actinin-4, Elongation factor 2 (squamous cell carcinoma of the lung), ME1 (non-small cell lung carcinoma), NFYC (squamous cell carcinoma of the lung), NY-ESO-1, GAGE-1,2,8, HERV-K-MEL, KK-LC-1, KM-HN-1, LAGE-1, MAGE-A2, MAGE-A6 (squamous cell lung carcinoma), Sp17, TAG-1, TAG-2, TRAG-3, XAGE-1b/GAGED2a (non-small cell lung cancer), c-myc, cyclin B1 Her2/Neu, MUC1, p53, p62, Survivin |
| Prostate cancer | DKK1, ENAH (hMena), Kallikrein 4, PSMA, STEAP1, PAP, PSA (prostate carcinoma), NY-ESO-1,, BAGE-1 (non-small cell lung carcinoma), GAGE-1,2,8 (non-small cell lunch carcinoma), GAGE-3,4,5,6,7 (lung squamous cell carcinoma and lung adenocarcinoma), HERV-K-MEL, KK-LC-1, KM-HN-1, LAGE-1, Sp17 |
| Kidney cancer | FGF5, Hepsin, Intestinal carboxyl esterase, M-CSF, RU2AS, hsp70-2 (renal cell carcinoma), Mannan-MUC-1 (renal cell carcinoma), MAGE-A9 (renal cell carcinoma) |
| Melanoma | Hepsin, ARTC1, B-RAF, beta-catenin, Cdc27, CDK4, CDK12, CDKN2A, CLPP, CSNK1A1, FN1, GAS7, GPNMB, HAUS3, LDLR-fucosyltransferase, MART2, MATN, MUM-1, MUM-2, MUM-3, neo-PAP, Myosin class I, PPP1R3B, PRDX5, PTPRK, N-ras, RBAF600, SIRT2, SNRPD1, Triosephosphate isomerase, OA1, RAB38/NY-MEL-1, TRP-1/gp75, TRP-2, Tyrosinase, Melan-A/MART-1, gp100/Pmel17, NY-ESO-1, BAGE-1, GAGE-1,2,8, GAGE-3,4,5,6,7 (cutaneous melanoma), GnTVf, HERV-K-MEL, KK-LC-1, KM-HN-1, LAGE-1, LY6K, MAGE-A1, MAGE-A6, MAGE-A10, MAGE-A12, MAGE-C2, NA88-A, Sp17, SSX-2, SSX-4, TRAG-3, TRP2-INT2g, pgk |
| Squamous cell carcinoma | CASP-8, p53, SAGE |
| Chronic myeloid leukemia | BCR-ABL, dek-can, EFTUD2, GAGE-3,4,5,6,7 |
| Acute lymphoblastic leukemia | ETV6-AML1, GAGE-3,4,5,6,7 |
| Acute myelogenous leukemia | FLT3-ITD, Cyclin-A1, GAGE-3,4,5,6,7 |
| Chronic lymphocytic leukemia | FNDC3B, GAGE-3,4,5,6,7 |
| Promyelocytic leukemia | pml-RARalpha, GAGE-3,4,5,6,7 |
| Multiple myeloma | MAGE-C1, NY-ESO-1, LAGE-1, HERV-K-MEL, KK-LC-1, KM-HN-1, Sp17 |
| B-cell lymphoma | D393-CD20 |
| Bladder carcinoma | BAGE-1, GAGE-1,2,8, GAGE-3,4,5,6,7, MAGE-A4 (transitional cell carcinoma of urinary bladder), MAGE-A6, SAGE, NY-ESO-1, LAGE-1, HERV-K-MEL, KK-LC-1, KM-HN-1, Sp17 |

TABLE 2-continued

Cancer type and TAAs

| Cancer type | Tumor associated antigen (TAA) |
| --- | --- |
| Head and neck cancer | BAGE-1 (head and neck squamous cell carcinoma), GAGE-1,2,8, GAGE-3,4,5,6,7, LY6K, MAGE-A3 (head and neck squamous cell carcinoma), MAGE-A6, SAGE |
| Esophageal cancer | GAGE-3,4,5,6,7 (Esophageal squamous cell carcinoma and esophageal adenocarcinoma), MAGE-A2, MAGE-A6, NY-ESO-1, LAGE-1, HERV-K-MEL, KK-LC-1, KM-HN-1, Sp17 |
| Brain cancer | TAG-1, TAG-2 |
| Pharynx cancer | TAG-1, TAG-2 |
| Tumors of the tongue | TAG-1, TAG-2 |
| Synovial cell sarcoma | NY-ESO-1, LAGE-1, HERV-K-MEL, KK-LC-1, KM-HN-1, Sp17 |
| Neuroblastoma | NY-ESO-1, LAGE-1, HERV-K-MEL, KK-LC-1, KM-HN-1, Sp17 |
| Uterine cancer | NY-ESO-1, LAGE-1, HERV-K-MEL, KK-LC-1, KM-HN-1, Sp17 |

Diagnostics

The peptides of the invention may be used in a variety of immunoassays for cancer and other diseases. The peptides of the invention can be produced with high quality control and are suitable as reagents for the purposes of detection of antigen in biological samples. By way of example and not limitation, peptides of the invention could be used as reagents in an ELISA assay to detect cancer antigen in a biological sample from a subject.

In one application, the peptides of this invention are used as a vehicle to improve the delivery of a diagnostic or imaging agent to cancer cells in vivo. For example, membrane permeabilization occurs only in the vicinity of a solid tumor due to the locally-acidic pH. Diagnostic or imaging agents that are also present in lipid vesicles as described herein increase access to the cancer cells due to the membrane pores formed by the peptides of this invention. Once the lower pH around the target cancer cell triggers the macromolecular assembly of the pore-forming peptides, a diagnostic agent that is stored as cargo within the lipid vesicle may be delivered specifically to the cancer cell (see also Example 14).

Alternatively, lipid vesicles containing the pore-forming peptides and a diagnostic or imaging agent can also contain a targeting agent that allows the lipid vesicle to bind to a target cell, thereby facilitating entry of the lipid vesicle into the target cell (e.g., endocytosis, such as via receptor-mediated endocytosis). Once in the target cell, lowering of the pH in the endosome would trigger release of the diagnostic agent into the cell.

Diagnosis of a disease condition, such as cancer, can be accomplished by detecting a reagent (e.g., a diagnostic agent, such as a fluorophore, a radiolabel, and an imaging agent (e.g., a PET- or MRI-detectable agent)) that is delivered via the pore forming peptides to the target cell (e.g., a cancer cell).

Pharmaceutical Compositions

The polynucleotides, polypeptides, lipid bilayers, and lipid vesicles described herein can be prepared as compositions that contain a pharmaceutically acceptable carrier, excipient, or stabilizer known in the art (*Remington: The Science and Practice of Pharmacy* 20th Ed., 2000, Lippincott Williams and Wilkins, Ed. K. E. Hoover), in the form of a lyophilized formulation, or as an aqueous solution. Acceptable carriers, excipients, or stabilizers are non-toxic to recipients at the employed dosages and concentrations, and may comprise buffers such as phosphate, citrate, and other organic acids; antioxidants including ascorbic acid and methionine; preservatives (e.g. octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The compositions (e.g., when used in the methods of the invention) generally comprise, by way of example and not limitation, an effective amount of a polynucleotide or polypeptide (e.g., an amount sufficient to induce an immune response or an amount sufficient to mitigate disease, alleviate a symptom of disease and/or prevent disease) of the invention (e.g., one or more of the peptides of Table 1, a polynucleotide encoding the peptide, and variants thereof having at least 85% sequence identity thereto, and analogs thereof.

The pharmaceutical composition of the present invention can further comprise additional agents that serve to enhance and/or complement the desired effect. By way of example, to enhance the efficacy of the one or more membrane permeabilizing peptides or fragments or combinations thereof administered as a pharmaceutical composition, the pharmaceutical composition may further comprise an adjuvant. Examples of adjuvants are provided herein.

Also by way of example and not limitation, if the one or more membrane permeabilizing peptides or fragments or combinations thereof of the invention is being administered to augment the immune response in a subject with cancer or suspected of having cancer, the composition can further comprise other therapeutic agents (e.g., anti-cancer, chemotherapeutic agents, and/or immunotherapy agents) Examples of immunotherapy agents include, e.g., an anti-CTLA-4 agent, an anti-PD-1 agent, an anti-PD-L1 agent, an anti-PD-L2 agent, a TNF-α cross-linking agent, a TRAIL cross-linking agent, an anti-CD27 agent, an anti-CD30 agent, an anti-CD40 agent, an anti-4-1 BB agent, an anti-GITR agent, an anti-OX40 agent, an anti-TRAILR1 agent, an anti-TRAILR2 agent, an anti-TWEAKR agent, an anti-TWEAK agent, an anti-cell surface lymphocyte protein agent, an anti-BRAF agent, an anti-MEK agent, an anti-CD33 agent, an anti-CD20 agent, an anti-HLA-DR agent, an anti-HLA class I agent, an anti-CD52 agent, an anti-A33 agent, an anti-GD3 agent, an anti-PSMA agent, an anti-Ceacan 1 agent, an anti-Galedin 9 agent, an anti-HVEM agent, an anti-VISTA agent, an anti-B7 H4 agent, an anti-HHLA2 agent, an anti-CD155 agent, an anti-CD80 agent, an anti-BTLA agent, an anti-CD160 agent, an anti-CD28 agent, an anti-CD226 agent, an anti-CEACAM1 agent, an anti-TIM3 agent, an anti-TIGIT agent, an anti-CD96 agent, an anti-CD70 agent, an anti-CD27 agent, an anti-LIGHT agent, an anti-CD137 agent, an anti-DR4 agent, an anti-CR5 agent, an anti-TNFRS agent, an anti-TNFR1 agent, an anti-FAS agent, an anti-CD95 agent, an anti-TRAIL agent, an anti-DR6 agent, an anti-EDAR agent, an anti-NGFR agent, an anti-OPG agent, an anti-RANKL agent, an anti-LTβ receptor agent, an anti-BCMA agent, an anti-TACI agent, an anti-BAFFR agent, an anti-EDAR2 agent, an anti-TROY agent, or an anti-RELT agent. For example, the immunotherapy agent may be an anti-CTLA-4 antibody or antigen-binding fragment thereof, an anti-PD-1 antibody or antigen-binding fragment thereof, an anti-PD-L1 antibody or antigen-binding fragment thereof, an anti-PD-L2 antibody or antigen-binding fragment thereof, a TNF-α cross-linking antibody or antigen-binding fragment thereof, a TRAIL cross-linking antibody or antigen-binding fragment thereof, an anti-CD27 antibody or antigen-binding fragment thereof, an anti-CD30 antibody or antigen-binding fragment thereof, an anti-CD40 antibody or antigen-binding fragment thereof, an anti-4-1BB antibody or antigen-binding fragment thereof, an anti-GITR antibody or antigen-binding fragment thereof, an anti-OX40 antibody or antigen-binding fragment thereof, an anti-TRAILR1 antibody or antigen-binding fragment thereof, an anti-TRAILR2 antibody or antigen-binding fragment thereof, an anti-TWEAKR antibody or antigen-binding fragment thereof, an anti-TWEAK antibody or antigen-binding fragment thereof, an anti-cell surface lymphocyte protein antibody or antigen-binding fragment thereof, an anti-BRAF antibody or antigen-binding fragment thereof, an anti-MEK antibody or antigen-binding fragment thereof, an anti-CD33 antibody or antigen-binding fragment thereof, an anti-CD20 antibody or antigen-binding fragment thereof, an anti-HLA-DR antibody or antigen-binding fragment thereof, an anti-HLA class I antibody or antigen-binding fragment thereof, an anti-CD52 antibody or antigen-binding fragment thereof, an anti-A33 antibody or antigen-binding fragment thereof, an anti-GD3 antibody or antigen-binding fragment thereof, an anti-PSMA antibody or antigen-binding fragment thereof, an anti-Ceacan 1 antibody or antigen-binding fragment thereof, an anti-Galedin 9 antibody or antigen-binding fragment thereof, an anti-HVEM antibody or antigen-binding fragment thereof, an anti-VISTA antibody or antigen-binding fragment thereof, an anti-B7 H4 antibody or antigen-binding fragment thereof, an anti-HHLA2 antibody or antigen-binding fragment thereof, an anti-CD155 antibody or antigen-binding fragment thereof, an anti-CD80 antibody or antigen-binding fragment thereof, an anti-BTLA antibody or antigen-binding fragment thereof, an anti-CD160 antibody or antigen-binding fragment thereof, an anti-CD28 antibody or antigen-binding fragment thereof, an anti-CD226 antibody or antigen-binding fragment thereof, an anti-CEACAM1 antibody or antigen-binding fragment thereof, an anti-TIM3 antibody or antigen-binding fragment thereof, an anti-TIGIT antibody or antigen-binding fragment thereof, an anti-CD96 antibody or antigen-binding fragment thereof, an anti-CD70 antibody or antigen-binding fragment thereof, an anti-CD27 antibody or antigen-binding fragment thereof, an anti-LIGHT antibody or antigen-binding fragment thereof, an anti-CD137 antibody or antigen-binding fragment thereof, an anti-DR4 antibody or antigen-binding fragment thereof, an anti-CR5 antibody or antigen-binding fragment thereof, an anti-TNFRS antibody or antigen-binding fragment thereof, an anti-TNFR1 antibody or antigen-binding fragment thereof, an anti-FAS antibody or antigen-binding fragment thereof, an anti-CD95 antibody or antigen-binding fragment thereof, an anti-TRAIL antibody or antigen-binding fragment thereof, an anti-DR6 antibody or antigen-binding fragment thereof, an anti-EDAR antibody or antigen-binding fragment thereof, an anti-NGFR antibody or antigen-binding fragment thereof, an anti-OPG antibody or antigen-binding fragment thereof, an anti-RANKL antibody or antigen-binding fragment thereof, an anti-LTβ receptor antibody or antigen-binding fragment thereof, an anti-BCMA antibody or antigen-binding fragment thereof, an anti-TACI antibody or antigen-binding fragment thereof, an anti-BAFFR antibody or antigen-binding fragment thereof, an anti-EDAR2 antibody or antigen-binding fragment thereof, an anti-TROY antibody or antigen-binding fragment thereof, or an anti-RELT antibody or antigen-binding fragment thereof. In some embodiments, the immunotherapy agent is an anti-cell surface lymphocyte protein antibody or antigen-binding fragment thereof, such as an antibody or antigen-binding fragment thereof that binds one or more of CD1, CD2, CD3, CD4, CD5, CD6, CD7, CD8, CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49, CD50, CD51, CD52, CD53, CD54, CD55, CD56, CD57, CD58, CD59, CD60, CD61, CD62, CD63, CD64, CD65, CD66, CD67, CD68, CD69, CD70, CD71, CD72, CD73, CD74, CD75, CD76, CD77, CD78, CD79, CD80, CD81, CD82, CD83, CD84, CD85, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD120, CD121, CD122, CD123, CD124, CD125, CD126, CD127, CD128, CD129, CD130, CD131, CD132, CD133, CD134, CD135, CD136, CD137, CD138, CD139, CD140, CD141, CD142, CD143, CD144, CD145, CD146, CD147, CD148, CD149, CD150, CD151, CD152, CD153, CD154, CD155, CD156, CD157, CD158, CD159, CD160, CD161, CD162, CD163, CD164, CD165, CD166, CD167, CD168, CD169, CD170, CD171, CD172, CD173, CD174, CD175, CD176, CD177, CD178, CD179, CD180, CD181, CD182, CD183, CD184, CD185, CD186, CD187, CD188, CD189, CD190, CD191, CD192, CD193, CD194, CD195, CD196, CD197, CD198, CD199, CD200, CD201, CD202, CD203, CD204, CD205, CD206, CD207, CD208, CD209, CD210, CD211, CD212, CD213, CD214, CD215, CD216, CD217, CD218, CD219, CD220, CD221, CD222, CD223, CD224, CD225, CD226, CD227, CD228, CD229, CD230, CD231, CD232, CD233, CD234, CD235, CD236, CD237, CD238, CD239, CD240, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD280, CD281, CD282, CD283, CD284, CD285, CD286, CD287, CD288, CD289, CD290, CD291, CD292, CD293, CD294, CD295, CD296, CD297, CD298, CD299, CD300, CD301, CD302, CD303, CD304, CD305, CD306, CD307, CD308, CD309, CD310, CD311, CD312, CD313, CD314, CD315, CD316, CD317, CD318, CD319, and/or CD320.

In some embodiments, the immunotherapy agent is an agent (e.g., a polypeptide, antibody, antigen-binding fragment thereof, a single-chain polypepytide, or construct) that binds a chemokine or lymphokine, such as a chemokine or lymphokine involved in tumor growth. For instance, the immunotherapy agent may be an agent (e.g., polypeptide, antibody, antigen-binding fragment thereof, single-chain polypepytide, or construct) that bind and inhibits the activity of one or more, or all, of CXCL1, CXCL2, CXCL3, CXCL8, CCL2 and CCL5. In some embodiments, the immunotherapy agent is an agent (e.g., a polypeptide, antibody, antigen-binding fragment thereof, a single-chain polypepytide, or construct) that binds and inhibits the activity of one or more, or all, of CCL3, CCL4, CCL8, and CCL22.

The immunotherapy agent may be capable of specifically binding one or more of the immunological targets described in Table 1 of Mahoney et al., *Cancer Immunotherapy*, 14:561-584 (2015), the disclosure of which is incorporated herein by reference in its entirety. For example, the immunotherapy agent may be an agent, such as an antibody or antigen-binding fragment thereof, that specifically binds one or more of OX40L, TL1A, CD40L, LIGHT, BTLA, LAGS, TIM3, Singlecs, ICOS, B7-H3, B7-H4, VISTA, TMIGD2, BTNL2, CD48, KIR, LIR, LIR antibody, ILT, NKG2D, NKG2A, MICA, MICB, CD244, CSF1R, IDO, TGFβ, CD39, CD73, CXCR4, CXCL12, SIRPA, CD47, VEGF, or neuropilin. In particular, the immunotherapy agent is an anti-PD-1 or anti-PDL1 antibody.

Additional examples of immunotherapy agents include, e.g., Targretin, Interferon-alpha, clobestasol, Peg Interferon (e.g., PEGASYS®), prednisone, Romidepsin, Bexarotene, methotrexate, Trimcinolone cream, anti-chemokines, Vorinostat, gabapentin, antibodies to lymphoid cell surface receptors and/or lymphokines, antibodies to surface cancer proteins, and/or small molecular therapies like Vorinostat.

Dosage and Administration

The pharmaceutical compositions used in this invention can be administered to a subject (e.g., a human) in a variety of ways. The compositions must be suitable for the subject receiving the treatment and the mode of administration. Furthermore, the severity of the disease or indication to be treated affects the dosages and routes. The pharmaceutical compositions used in this invention may be administered orally, buccally, sublingually, parenterally, intravenously, subcutaneously, intramedullary, intranasally, as a suppository, using a flash formulation, topically, intradermally, subcutaneously, via pulmonary delivery, via intra-arterial injection, ophthalmically, optically, intrathecally, or via a mucosal route.

In general, the dosage of a pharmaceutical composition or the active agent in a pharmaceutical composition may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g, 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition may also be administered as in a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the patient per unit day (e.g., 0.1-10 mg/kg/day).

The dosage regimen may be determined by the clinical indication being addressed, as well as by various patient variables (e.g., weight, age, sex) and clinical presentation (e.g., extent or severity of disease). Furthermore, it is understood that all dosages may be continuously given or divided into dosages given per a given time frame. The composition may be administered, for example, every hour, day, week, month, or year.

Kits

The invention also provides kits for use in the instant methods. Kits of the invention include one or more containers comprising, for example, membrane permeabilizing polypeptides, polynucleotides encoding one or more membrane permeabilizing peptides, combinations thereof, fragments thereof, lipid bilayers or lipid vesicles containing the polynucleotides and/or peptides of the invention and instructions for use in accordance with any of the methods of the invention described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g. the container may be an intravenous solution bag or a vial having a stopper pierceable by a hypodermic injection needle). The container may also have a sterile access port (e.g. the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1

Peptide Library Design and Synthesis

The peptide library was a one-bead-one-peptide library, synthesized using a split and recombine approach described in detail previously (32, 34, 35). The library members were synthesized on Tentagel Megabead MB $NH_2$ resin beads (Raap Polymere MB300002), coupled to it by a UV-cleavable photo linker, 4-(4-[1-(9-Fluorenylmethyloxycarbonylamino)ethyl]-2-methoxy-5-nitrophenoxy) butanoic acid. After synthesis, sidechains were deprotected with a mixture of trifluoroacetic acid and scavengers (36). Beads were then washed extensively and stored dry at −20° C. prior to use.

To cleave the photolinker and release the library members, beads were first suspended in methanol and dispersed onto a glass plate. The beads were dried thoroughly and then exposed to UV light at 365 nm for 4 hours with illumination from plate top and bottom. One day prior to screening, beads were placed into the wells of a 96-well plate, one bead per well. Water and hexafluoroisopropanol (25 uL each) were added to each well, and the plates were exposed to 365 nm UV light for an additional 3 hours, releasing and extracting the peptide while also evaporating the solvent. Finally, 25 uL of water was added to each well and plates were incubated overnight for peptide solubilization. About 0.5 nmol of peptide was extracted from each bead, as quantified by tryptophan fluorescence.

The peptide MelP5 is a highly potent, gain-of-function variant of the cytolytic bee venom peptide melittin that was discovered in a high-throughput screen of a library that used melittin as a template (32). While the melittin library was screened only for dramatically increased potency of small molecule release, it was later showed that MelP5, the most potent gain-of-function peptide discovered, also releases macromolecules from vesicles at low peptide concentration (33). Among the many known membrane permeabilizing peptides, MelP5 is unique its ability to induce the passage of dextrans up to a molecular weight 40,000 through bilayers. MelP5 is unstructured in solution, but it folds into an amphipathic α-helix in the presence of membranes, into which it inserts, leading to macromolecule-sized membrane disruption at low peptide-to-lipid ratios, P:L≤1:500.

Previously, pH sensitive, macromolecular pore-forming peptides were rationally designed (26) by encoding pH-sensing motifs, based on the sequences of the pH-sensitive membrane active peptides GALA (27) and pHLIP (10), into the pH-insensitive, macromolecular pore-forming motif in MelP5 (33). The designed peptides, named MelP5_Δ4 and MelP5_Δ6 (see Table 1), had four or six of the residues along the polar face of the putative amphipathic helix changed to glutamate or aspartate to impart pH sensitivity. Placement and spacing of the acidic residues were based on their helical spacings in GALA and pHLIP. These rationally designed peptides gained pH sensitivity, as they permeabilized membranes only at pH<5.0. But at the same time, they lost the ability to form macromolecular-sized pores (26), demonstrating that the properties of MelP5, GALA, and pHLIP are only partially additive.

Here, the same goal was approached with combinatorial chemistry and high throughput screening, instead of rational design. Specifically, an iterative 18,432-member library was designed using MelP5 as a template, as shown in FIG. 1, creating a second generation library that was screened orthogonally for peptides that release macromolecules from lipid vesicles at pH 5, but have little or no membrane permeabilizing activity at pH 7.

In the library, the amino acids at nine positions were varied, as seen in FIG. 1. Unlike MelP5_Δ4 and MelP5_Δ6, which had a fixed number and pattern of helically spaced acidic residues, the library contained peptides with 0 to 6 acidic residues distributed in all possible patterns along the face of the alpha helix. The criteria for placement of acidic residues were as follows: i) maximize the number of i to i+3, i to i+4 and i to i+7 α-helical spacings between acidic groups to maximize the electrostatic repulsion between them at neutral pH, and prevent helix formation. For some library members, it was expected that such electrostatic repulsion among the acidic sidechains would prevent binding and membrane insertion at pH 7 but allow it at pH 5. This pattern also enables library members to form amphipathic helices in which the protonation state of the acidic residues can make a significant contribution to helical propensity and membrane insertion; ii) retain basic residues at positions 7 and 21 because it was hypothesized that changing them to acidic residues in MelP5_Δ4 and MelP5_Δ6 (26) may have altered the peptide function; iii) retain overlap between the polar face of the MelP5 helix and the positions of the new acidic residues; iv) reduce hydrophobicity as little as possible to maintain the propensity of the helix to partition into membranes; v) avoid replacing any residues known to be critical to the activity of MelP5, specifically A10, P14,L16, and A23 (32); and vi) avoid replacing tryptophan 19 because it is useful for concentration determination and as an optical probe of structure. With these criteria in mind, both glutamate and aspartate were allowed to appear at six positions: A4, V8, T11, G12, A15 and S18, giving the distribution shown in FIG. 1. The native residue was also allowed in each of these positions, and hydrophobic leucines were allowed to occur at positions A4, G11 and A18 and a somewhat hydrophobic alanine at T11 to modulate hydrophobicity. To potentially compliment the pH sensitivity of the acidic residues, the native lysines at positions 7 and 21 were allowed to also be histidine. Lysine will be cationic at all pH values below 8.5, whereas histidine will be cationic only below its $pK_a$ of ~6.5.

Previously, it was shown that the presence or absence of polar residues at the boundary of the polar-nonpolar faces is a critical feature of MelP5 (32). Specifically, the native T10 in the first generation library was replaced with alanine, which narrows the polar face substantially, shown in FIG. 1. In the current library, A10 on the N-terminal half of the peptide was preserved, and position 17 was allowed to vary between hydrophobic isoleucine and polar glutamine. Position 17 defines the cutoff between the polar and non-polar faces on the C-terminal half of the helix.

There are 18,432 unique, 26-residue, MelP5 variants in the library. All library members share at least 17 residues of 26 in common with MelP5 such that the minimum identity is 73%. If it is assumed that D and E are equivalent, there are 64 different patterns of acidic residues in the library. Assuming D and E are unique gives 729 different patterns. From the library design in FIG. 1, the following abundance values were calculated: 2.8% of library members have 6 acidic residues (1 pattern of 64), 13.8% have 5 acidic residues (6 patterns), 28.5% have 4 acidic residues (14 patterns), 30.6% have 3 acidic residues (20 patterns), 18.1% have 2 acidic residues (14 patterns), 5.6% have 1 acidic residue (6 patterns) and 0.7% have 0 acidic residues (1 pattern).

The library was synthesized as a one-bead, one-peptide library using a well-established split and recombine approach (32, 34, 35). Quality control for the synthesis was done using HPLC, MALDI mass spec, and Edman degradation on multiple individual beads. These methods showed that every bead examined contained predominantly a single pure sequence and that each sequence observed was, in fact, an expected member of the library. Each 0.3 mm polystyrene solid phase peptide synthesis bead releases about 0.5 nmol of one single sequence as described above.

Example 2

Vesicle Preparation

Large unilamellar vesicles for leakage assays were prepared as previously described (37) in 100 mM potassium chloride, with 10 mM sodium phosphate or 10 mM sodium acetate buffer. For small molecule leakage, lipids, dried from chloroform, were resuspended in buffer made of: 12.5 mM ANTS, 45 mM DPX, 5 mM HEPES, and 20 mM sodium chloride. For macromolecular leakage assays, lipids were resuspended in buffer with 1 mg/ml TAMRA-biotin-dextran (TBD). Lipid suspensions were frozen and thawed ten times and then extruded 10 times using a 0.1 um pore size Nuclepore polycarbonate filter (38). After extrusion, external ANTS and DPX were removed by gel filtration with Sephadex G100. External TBD was removed using streptavidin agarose resin.

Example 3

Small Molecule Leakage Assay

Lipid vesicles with entrapped ANTS and DPX were diluted into wells of a 96 well plate containing peptide. After 30 minutes, vesicle permeabilization was measured by an increase in ANTS fluorescence, with excitation at 350 nm and emission at 519 nm. Fractional leakage was quantified using Equation 1:

$$\text{Fraction } ANTS \text{ Leakage} = \frac{I - I_{background}}{I_{triton} - I_{background}}$$

Here, I is the intensity at 30 min, $I_{background}$ is the intensity of a control with vesicles only, and $I_{triton}$ is the intensity in the presence of vesicles and 0.1% v/v of the detergent Triton X-100 added to solubilize the vesicles and release the ANTS.

Example 4

Macromolecular Leakage Assay

As described previously (33), 40 nM Alexafluor488-labelled streptavidin (SA) was added to a solution of vesicles with entrapped TBD. This solution was added to wells of a 96-well plate containing peptide, and the plate was incubated for 60 min. Release of the 40 kDa dextran enables TBD-SA complex formation, which leads to quenching of the AF488 fluorescence (excitation 495 nm, emission at 519 nm) by TAMRA. The fraction of macromolecule leakage was determined by Equation 2:

$$\text{Fraction } TBD \text{ Leakage} = \frac{I_{background} - I}{I_{background} - I_{triton}}$$

where I is the intensity at 60 min, $I_{background}$ is the intensity of a vesicle control with no peptide, and $I_{triton}$ is the intensity in the presence of vesicles and 0.1% v/v of the detergent Triton X-100, added to solubilize the vesicles and release the ANTS.

Example 5

High Throughput Screening

In the orthogonal high throughput screen, the two assays described above were combined and used in 96-well format as follows.

Step 1: Individual beads were separated into the wells of a plate and peptides were extracted into a small volume of water as described above. Each bead releases about 0.5 nmol of one peptide sequence from the library.

Step 2: Aliquots of peptides in water from the plate in Step 1 were added to wells of a second plate, followed by addition of 1 mM lipid vesicles in 100 μl of sodium phosphate buffer at pH 7. These vesicles contained the 350 Da fluorophore ANTS and its quencher DPX, entrapped at mM concentrations. After this step, the nominal peptide concentration was 5 μM and the peptide to lipid ratio was roughly 1:200. Leakage, if it occurs, causes an increase in fluorescence of ANTS. A few wells contained controls: vesicles only, 1 nmol of the peptide MelP5 (P:L=1:100), 4 nmol of MelP5 (P:L=1:25), or 0.1% v/v of the detergent Triton X-100. The latter two should completely permeabilize the vesicles.

Step 3: After 30 minutes of incubation, ANTS fluorescence was measured for each well to quantitate small molecule release using equation 1.

Step 4: Next, to the same wells, a different preparation of vesicles was added. These vesicles have entrapped 40 kDa TBD and external Alexafluor488 streptavidin. The TBD vesicles were in sodium acetate buffer at pH 4 so that the final pH in each well was 5.0. This second addition of vesicles increased the total volume to 200 μl which decreased peptide to 2.5 μM and decreased ANTS vesicle concentration to 0.5 mM. The new TBD vesicles were present at 1.5 mM so that the total peptide to total lipid ratio was roughly about 1:800.

Step 5: After 60 minutes, the intensity of the AF488-streptavidin was measured to quantitate macromolecule release, which is calculated with equation 2. This orthogonal and sequential screen gives two measurements that are used to identify peptides with the desired properties: i) Small molecule release at pH 7 and P:L=1:200; ii) Macromolecule release at pH 5 and P:L=1:800.

The library was screened for peptides that simultaneously i) cause little or no membrane permeabilization at pH 7, even for small molecule reporters and high peptide concentrations, and ii) cause macromolecule passage across bilayers at pH 5, at low peptide concentrations. Two different assays, described above, were used in tandem to achieve these aims. One was an assay for release of ANTS, a small molecule, shown in FIG. 2A, performed at pH 7. The second was an assay for release of 40 kDa TBD, conducted at pH 5, shown in FIG. 2B. These two assays can be performed in parallel or in series in the same samples because there is no relevant spectral overlap between ANTS fluorescence (ex/em 350/519), and AF488 fluorescence (ex/em 488/505 nm). The ANTS/DPX assay was conducted at a nominal peptide to lipid ratio of 1:200 at pH 7, and the dextran leakage assay was performed at nominal P:L=1:800, at pH 5. Because the peptide release from individual beads varies, P:L could vary between individual wells by a factor of 2 or more.

15,000 library members were screened using the orthogonal high throughput screen, covering about 80% of the library's sequence space. FIG. 3 shows the ability of each screened peptide to cause small molecule leakage at pH 7 and macromolecular leakage at pH 5. The results are presented in the form of a scatterplot colored according to point density from light grey (highest density) to black (lowest density). Because there were vesicle batch-to-batch variations in the raw intensity values for each assay along the duration of the screen, all values were plotted in FIG. 3 as plate-by-plate Z-values; the points plotted are the number of standard deviations from the plate mean, on each axis. The density of points on the Y-axis is centered on zero because the distribution of dextran leakage has a symmetrical Gaussian shape. The distribution of points on the X-axis is offset from zero because ANTS leakage at pH 7 is asymmetric; abundant library members cause >80% leakage of ANTS at pH 7.

Four points provide useful landmarks. The activity of 1 nmol and 4 nmol of the template MelP5 under the conditions of the screen are indicated in FIG. 3, to compare with 0.5 nmol of each library peptide. Values are shown for blank wells with no peptide and for 0.1% v/v Triton X100, which solubilizes all vesicles. One nmol of MelP5 causes high small molecule permeabilization and partial macromolecule release at all pH values. Four nmol of MelP5 (P:L=1:100) and 0.1% v/v of Triton X-100 each cause essentially complete release of both types of probes. The activities of most library members are centered on the light grey area in FIG. 3; on average, they have MelP5-like high leakage of ANTS at pH 7 and moderate leakage of dextran at pH 5. The center of the light grey area corresponds to ~85% ANTS leakage and ~30% dextran leakage.

The peptides of interest here are closest to the upper left corner of FIG. 3. These peptides have low small molecule permeabilization at pH 7 (P:L=1:200) and high macromolecule permeabilization at pH 5 (P:L=1:800). Ten library members, shown by stars in FIG. 3, were selected from within this region, and these peptides were sequenced using Edman degradation. Their sequences are shown in Table 1. Data presented herein demonstrates that these selected peptides have exactly the properties sought in the screen. Thus, the strategy was successful.

Sequence analysis of positives. The positive sequences have many features in common with one another, demonstrating the identification of a family of closely related sequences with a novel, shared activity. P-values were calculated against a null hypothesis determined by the abundance of the particular residue, class, or motif in the library, using exact binomial statistics. Every positive peptide has 5 or 6 acidic residues out of six possible ($p<1\times10^{-5}$). Positions 4 and 8 are acidic in all positives ($p=0.002$ and $0.007$, respectively). In the remaining four positions that could have acidic groups, 11, 12, 15, and 18, eight of the ten peptides have three acidic residues and one other non-acidic residue and two have six acidic residues. Of the 9 possible i to i+3, i to i+4, and i to i+7 helical spacings of acidic groups available, the positive peptides have an average of 6.5 (range 5-9). The constancy of the acidic residue abundance supports the hypothesis, discussed earlier, that pH-triggered membrane activity is determined mostly by the coupling between electrostatic repulsion, and the formation of the amphipathic helix as it relates membrane binding (see measurements of helix content below).

Among the 52 selected acidic residues, there was a strong preference for glutamate with 36 glutamates selected compared to 16 aspartates ($p=0.007$). The preference for E over D is even more striking in the first two and last two possible positions, where 26 of 33 acidic residues were glutamate ($p=0.001$). It is not currently known why this preference exists, but the hypothesis is that the longer sidechain of glutamate enables more conformational flexibility of the sidechains by which the electrostatic effects can be modulated, either between acidic groups or in the interactions of acidic residues with basic residues. When an acidic residue was possible but not selected, the selected residues included both native residues and the more hydrophobic residues possible, indicating no strong preference for the native residues at positions 11, 12, 15, and 18. Similarly, 9 lysines and 11 histidines were selected in positions 7 and 21, with no obvious preference or pattern. In fact, all possible patterns (KK, HH, HK, and KH) were observed in the 10 positives. The identity of the basic sidechains and their charge state at pH 7 are of little consequence to the function of these peptides.

In position 17, where the native, hydrophobic isoleucine and the polar glutamine were possible, it was found that the native residue was replaced with glutamine in 10 of 10 peptides ($p=0.002$). The current lack of explicit structure-function relationships in these membrane active peptides makes it difficult to know exactly how this glutamine contributes to activity at this time, but it is hypothesized that its hydrogen bonding capabilities may enable lateral interactions between peptides in the bilayer.

There are interesting comparisons among the positive sequences selected from this library, which have the desired property of macromolecular poration at pH 5, and the rationally designed sequences MelP5_Δ4 and MelP5_Δ6, which have a lower pKa and do not allow macromolecules across membranes. The rational and selected peptides are similar in that both had 4-6 acidic residues with helical spacings. Some residues overlap, including the acidic residues replacing V8, T11 and S18 in both families. The rationally designed peptides have 3 or 5 helical spacings between acidic residues, while the selected peptides have 5-9, but there is overlap. In any case, fewer helical spacings should theoretically lead to a higher pKa whereas the designed peptides actually had a lower pKa than the selected ones. One or both basic residues were replaced in the designed peptides, whereas these positions only contained basic residues in the library because it was hypothesized that favorable electrostatic interactions with the basic residues could abrogate acidic repulsions in the library-selected peptides. Furthermore, the designed peptides always had isoleucine in position 17, while the selected peptides always had glutamine at position 17. Isoleucine was available at position 17 in the library, but was never selected. It is currently not possible to explain or predict these behaviors in molecular terms, effectively demonstrating the power of synthetic molecular evolution.

Verification of positive peptides. Since the selected peptides are very similar to each other, a subset of them were synthesized and purified for detailed validation. Tested peptides included four representative sequences with five acidic residues, pHD24, pHD34, pHD108 and pHD118 as well as pHD15, one of the two with six acidic residues. Because there is interest in pH-triggered macromolecule release at low pH, the positive peptides were validated with the macromolecular release assay using 40 kDa dextran and 53 kD streptavidin, described above. Dextran leakage was measured as functions of peptide concentration and pH using vesicles made from phosphatidylcholine lipids.

Figure 4A:
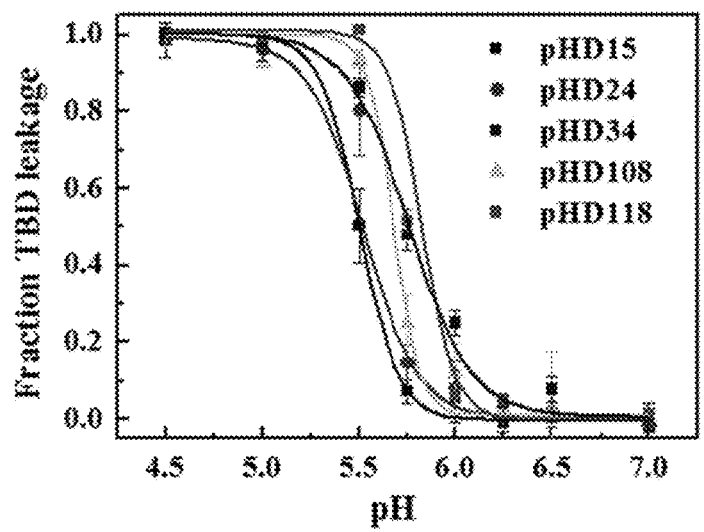
FIGS. 4A-4B are graphs depicting macromolecule leakage compared to pH and concentration of peptides.
Figure 4B:
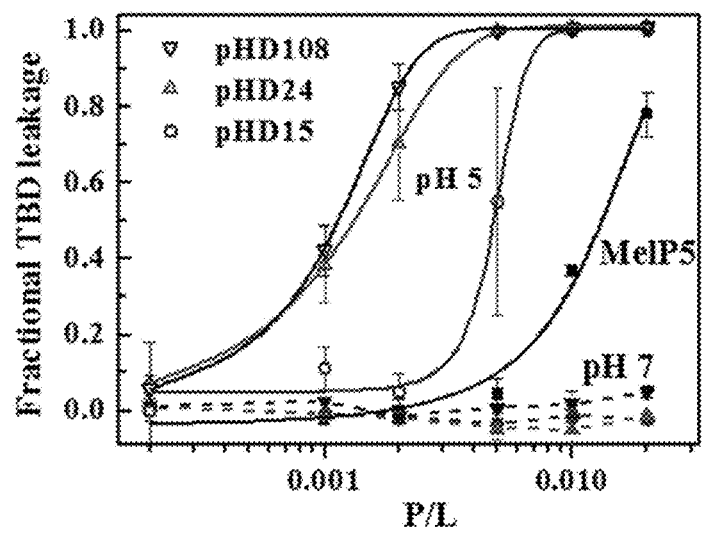

The leakage of 40 kDa dextran from lipid vesicles at P:L=1:200 as a function of pH is shown for these peptides in FIG. 4A. At this concentration, all of the selected peptides cause 100% dextran release at pH 5 and no leakage at pH 7, as desired. Activity occurs only as pH is decreased into the range of pH 5.5 to 6. The apparent pKa values for the five peptides are similar, ranging from 5.5 to 5.8, with pHD15 having the lowest apparent pKa value, consistent with it having one more acidic residue. This activity is novel and unexpected, as there are no other peptides known, except for MelP5 33, that release macromolecules from lipid vesicles at such low P:L ratios under any conditions. These synthetically evolved peptides have a pH-triggered version of this activity, and release macromolecules at pH 5 even better than MelP5 does at any pH.

Dextran release at pH 5 and pH 7 as functions of peptide concentration (expressed as peptide to lipid ratio, P:L) is shown in FIG. 4B for pHD15, pHD24, and pHD108. The dashed lines show that there is no activity at pH 7, as desired, even at peptide to lipid ratios as high as 1:50. However, at pH 5, the selected peptides induce substantial macromolecule leakage, with 50% leakage activity at peptide to lipid ratios of 1:900 for pHD108 and 1:750 for pHD24. pHD15, which has six acidic residues, is the least active of the positive peptides tested, with 50% release at P:L=1:600. While MelP5 has been shown to release a 10,000 Da dextran at similar concentrations (33), it releases the 40,000 Da dextran used in this work at ~P:L=1:100. Taken together, these results show the successful identification of peptides that are significantly more active than MelP5 and are triggered to act only in acidic pH environments.

Example 6

Circular Dichroism Spectroscopy

Peptide secondary structure in the presence of vesicles as a function of pH was studied by circular dichroism spectroscopy. Example CD spectra for pHD108 at P:L=1:200 are seen in FIG. 5A and show a pH-triggered transition from random coil to α-helical structure with an effective pKa around 5.5. Circular dichroism was measured in a JASCO 810 spectropolarimeter. Samples in buffers of various pH were prepared by mixing peptide and vesicle solutions, each prepared at the needed pH. Spectra were collected on samples of 2 mM vesicles and 10 μM peptide in 1 mm path rectangular quartz cuvette after 1 hour of equilibration.

Example 7

Tryptophan Fluorescence

Membrane partitioning was assessed at various pH values using tryptophan fluorescence in a Fluololog-3 fluorometer (Jobin Yvon). Peptide and lipid solutions were prepared at individual pH values and tryptophan fluorescence spectra were measured after 60 minutes of incubation. Excitation was fixed at 280 nm (slit 5 nm) and emission was collected from 300 to 450 nm (slit 5 nm). For assessment of binding versus pH, intensities were corrected for the effect of pH on the intensity of free tryptophan.

Figure 5B:
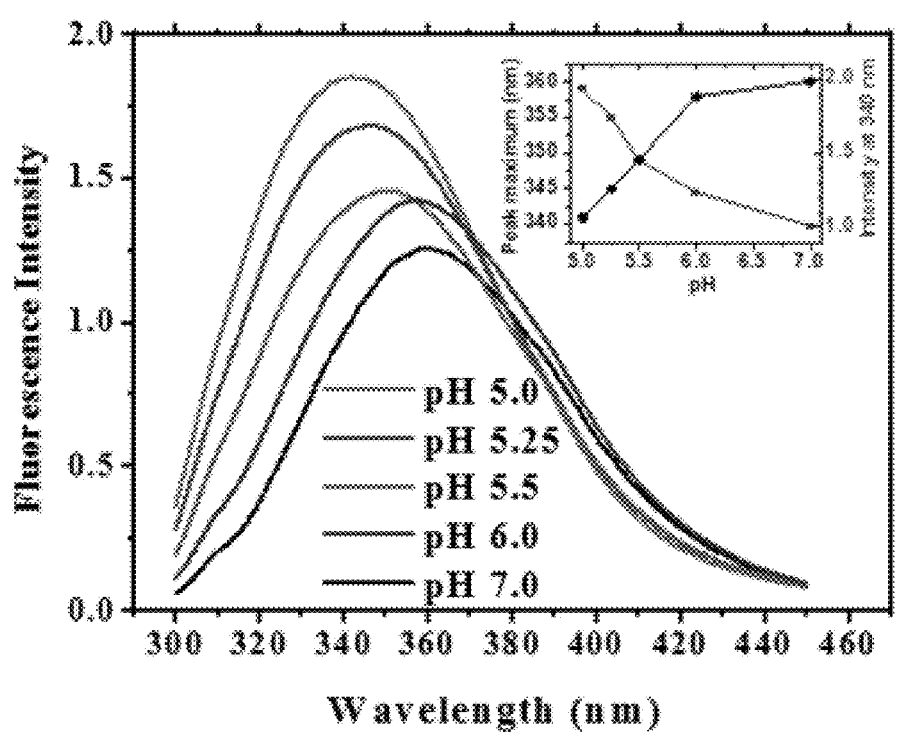

Tryptophan fluorescence was measured as a function of pH at P:L=1:200, which provides a measure of membrane partitioning. Like the circular dichroism spectra, example fluorescence spectra for pHD108, as seen in FIG. 5B, also show a sharp transition from lower intensity emission at 360 nm to higher intensity and 340 nm emission maximum, consistent with a transition from weak to strong membrane partitioning over the expected pH range of 5-6. FIGS. 6A-6C directly compare the pH-dependence of macromolecule leakage, helicity and tryptophan fluorescence for three peptides at P:L=1:200 and shows that they are very similar, with $pK_a$ of 5.5-5.8, consistent with the hypothesis that leakage, helicity, and binding are coupled.

Example 8

Cargo Delivery in Cell Culture Via Plasma Membrane

Cells growing in culture dishes are one of the most widely used experimental tools in biosciences. Their usefulness may be significantly increased by the ability to routinely deliver to the cell cytosol molecules such as metabolites, carbohydrates, peptides, proteins (enzymes, antibodies, nanobodies), imaging agents, and polynucleotides (RNA and DNA).

The pH-sensitive peptides of this invention form macromolecule-sized pores in membranes at acidic pH but are essentially inert at pH 7 or higher. In one application, the pHD peptides shown in Table 1, variants or analogs are added to a cell culture along with a cargo, macromolecular or otherwise. At the appropriate time, the pH of the solution is decreased temporarily to activate the pH-sensitive peptides, enabling delivery of the added cargo through pores in the membrane. Following the transient pH dependent delivery, the pH is increased. Alternatively, the external solution is exchanged with one of near neutral pH to reverse pore formation and enable the living cells to be studied.

In another application, pHD peptides shown in Table 1 are used to deliver a dye-labelled nanobody, such as a single-chain fc molecule, that has binding specificity for a particular phosphorylated receptor tyrosine kinase. Delivery of such a reagent to cells enables confocal fluorescence microscopy to be used for real-time monitoring of the kinase activation state within a living cell. In this application, a transition from cytosolic, diffuser nanobody to membrane-bound nanobody signifies the presence of the phosphorylated kinase domain and would enable its quantitation.

Example 9

Cargo Delivery in Cell Culture Via Endocytosis

Cargo molecules, including macromolecules, may be directed to endosomal uptake pathways in eukaryotic cell culture by conjugation to cell penetrating peptides, receptor ligands, or other molecules. The pH-sensitive peptides of this invention form macromolecule-sized pores in membranes at acidic pH but are essentially inert at physiological pH of 7 or higher. In one application, the pHD peptides shown in Table 1 or variants or analogs thereof are added to cell culture media along with a cargo, macromolecular or otherwise, that is directed to uptake pathways or is captured by fluid phase entrapment. pHD peptides shown in Table 1 or variants or analogs thereof may be directed to the endosome specifically or captured by fluid phase entrapment. Upon endosomal acidification, which is an early step in endosomal maturation, the co-endocytosed pH-sensitive peptides enable or enhance delivery of the cargo.

The pHD peptides shown in Table 1 may be used to deliver or improve the delivery of a specific kinase that is directed to the endosomal uptake pathway by conjugation to a cell penetrating peptide, such as TAT. The kinase cargo alters the phosphorylation state of a cellular substrate, enabling the changes in downstream signaling to be studied in the laboratory.

Example 10

Improved Transfection Efficiency by Endosomal Lysis

Transfection of eukaryotic or prokaryotic cells requires delivery of a polynucleotide (RNA or DNA) to the cells. This is currently accomplished with the help of cationic lipid kits, such as Lipofectamine, or peptides or polymers, which form complexes with anionic polynucleotides enabling their uptake into cells. In practice, transfection efficiencies remain low in most cell types and are near zero in others.

The poly-anionic nature of the pHD peptides shown in Table 1 enables their co-complexation with cationic transfection reagents and allows the pHD peptides to be uptaken along with polynucleotides and cationic transfection reagents. Upon acidification of endosomally uptaken complexes, pHD peptides may permeabilize endosomal membranes, enabling more efficient delivery of the polynucleotide to the cell cytosol and nucleus.

The peptides of this invention may be included in a kit that also provides a cationic transfection reagent, or the peptides may be made available as an auxiliary reagent for researchers desiring to improve the efficiency of transfection in cell culture.

Example 11

Cargo Delivery In Vivo by Endocytosis

Cargo molecules, including but not limited to therapeutic or imaging agents, may be directed to generic endosomal uptake pathways in vivo by conjugation to cell penetrating peptides, receptor ligands, or other molecules. Targeting to specific cell types in vivo may be accomplished with receptor ligands, for example. In one application, pHD peptides shown in Table 1 or variants or analogs thereof are mixed with or conjugated to cargoes to be delivered. pHD peptides are directed to the uptake pathways in the same cell types using the same ligands; alternatively, the pHD peptides or variants or analogs thereof are captured by fluid phase entrapment. Upon endosomal acidification, the pH-activated peptides enable or improve delivery of the intended cargo.

In another application, the pHD peptides shown in Table 1 or variants or analogs thereof may be used to deliver or to improve the delivery of a specific kinase that is directed to the endosomal uptake pathway by conjugation to a cell penetrating peptide, such as TAT. The kinase cargo may alter the phosphorylation state of a cellular substrate and may enable the changes in downstream signaling to be studied.

Example 12

Cancer-Specific Cytolytic Activity

Due to severely altered metabolic activity, the local pH in the vicinity of solid tumors is acidic. This property has been used to activate unrelated pH-sensitive membrane active peptides (10-12).

In one application, the peptides of the invention are used as a cell-killing therapeutic that is triggered to be active only in the vicinity of a solid tumor by the locally-acidic pH. As a therapeutic, these peptides have advantages over traditional chemotherapies in that cancer cells are much less likely to develop resistance. Furthermore, massive cell lysis releases immunogenic oncoproteins, enabling an improved immune response not available after traditional chemotherapy in which cells undergo apoprtosis rather than lysis.

Example 13

Cancer-Specific Chemosensitization

In one application, the peptides of this invention are used as enhancing agents to improve the delivery of one or more separate therapeutics to cancer cells in vivo. Membrane permeabilization occurs only in the vicinity of a solid tumor due to the locally-acidic pH. A chemotherapeutic agent that is also present has increased access to cancer cells due to membrane pores formed by the peptides of this invention. Drug efflux pumps, which drive much of the resistance of cancer cells to chemotherapeutics, may be inactivated or counteracted by direct permeabilization of the cell plasma membrane.

Example 14

Cancer-Specific Diagnostics or Imaging

In one application, the peptides of this invention are used as a vehicle to improve the delivery of a diagnostic or imaging agent to cancer cells in vivo. Membrane permeabilization occurs only in the vicinity of a solid tumor due to the locally-acidic pH. Diagnostic or imaging agents that are also present have increased access to the cancer cells due to the membrane pores formed by the peptides of this invention. An efficient two-photon excitable dye may be delivered specifically to cancer cells in this way, enabling the direct whole body fluorescent visualization of the tumor with deep penetrating two-photon excitation.

Example 15

Cancer-Specific Cytolysis, Chemosensitization, and Therapeutics

In one application, the peptides of this invention simultaneously have multiple synergistic properties that are directly related to their ability to form macromolecule-sized pores in membrane in a pH-sensitive manner. Membrane permeabilization by pHD peptides occurs in the vicinity of a solid tumor only due to the locally-acidic pH. Pore formation has direct cytolytic activity on cancer cells and at the same time enhances the delivery of one or more therapeutic, diagnostic and/or imaging agents that is also present.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. All publications, patents, and patent applications mentioned in the above specification are hereby incorporated by reference to the same extent as if each individual publication, patent or patent application was specifically and individually indicated to be incorporated by reference in its entirety.

Other embodiments are within the claims.

REFERENCES

1. Kakudo, T.; Chaki, S.; Futaki, S.; Nakase, I.; Akaji, K.; Kawakami, T.; Maruyama, K.; Kamiya, H.; Harashima, H. Transferrin-modified liposomes equipped with a pH-sensitive fusogenic peptide: An artificial viral-like delivery system. *Biochemistry* 2004, 43 (19), 5618-5628.
2. Oliveira, S.; van Rooy, I.; Kranenburg, O.; Storm, G.; Schiffelers, R. M. Fusogenic peptides enhance endosomal escape improving siRNA-induced silencing of oncogenes. *Inter. J. Pharamaceut.* 2007, 331 (2), 211-214.
3. Kullberg, M.; Owens, J. L.; Mann, K. Listeriolysin O enhances cytoplasmic delivery by Her-2 targeting liposomes. *Journal of Drug Targeting* 2010, 18 (4), 313-320.
4. Lam, J. K. W.; Liang, W.; Lan, Y.; Chaudhuri, P.; Chow, M. Y. T.; Witt, K.; Kudsiova, L.; Mason, A. J. Effective endogenous gene silencing mediated by pH responsive peptides proceeds via multiple pathways. *J. Control. Release* 2012, 158 (2), 293-303.
5. Shai, Y.; Oren, Z. From "carpet" mechanism to de-novo designed diastereomeric cell-selective antimicrobial peptides. *Peptides* 2001, 22 (10), 1629-1641.
6. Kauffman, W. B.; Fuselier, T.; He, J.; Wimley, W. C. Mechanism Maters: A Taxonomy of Cell Penetrating Peptides. *Trends Biochem. Sci.* 2015, 40 (12), 749-764.
7. Komin, A.; Russell, L. M.; Hristova, K. A.; Searson, P. C. Peptide-based strategies for enhanced cell uptake, transcellular transport, and circulation: Mechanisms and challenges. *Adv. Drug Deliv. Rev.* 2016.
8. Wimley, W. C.; Hristova, K. Antimicrobial Peptides: Successes, Challenges and Unanswered Questions. *J. Membr. Biol.* 2011, 239 (1-2), 27-34.
9. Soman, N. R.; Baldwin, S. L.; Hu, G.; Marsh, J. N.; Lanza, G. M.; Heuser, J. E.; Arbeit, J. M.; Wickline, S. A.; Schlesinger, P. H. Molecularly targeted nanocarriers deliver the cytolytic peptide melittin specifically to tumor cells in mice, reducing tumor growth. *Journal of Clinical Investigation* 2009, 119 (9), 2830-2842.
10. Andreev, O. A.; Engelman, D. M.; Reshetnyak, Y. K. pH-sensitive membrane peptides (pHLIPs) as a novel class of delivery agents. *Molecular Membrane Biology* 2010, 27 (7), 341-352.
11. Pantaleo, M. A.; Nannini, M.; Lopci, E.; Castellucci, P.; Maleddu, A.; Lodi, F.; Nanni, C.; Allegri, V.; Astorino, M.; Brandi, G.; Di Battista, M.; Boschi, S.; Fanti, S.; Biasco, G. Molecular imaging and targeted therapies in oncology: New concepts in treatment response assessment. A collection of cases. *International Journal of Oncology* 2008, 33 (3), 443-452.
12. Gillies, R. J.; Robey, I.; Gatenby, R. A. Causes and consequences of increased glucose metabolism of cancers. *J. Nucl. Med.* 2008, 49 Suppl 2, 24S-42S.
13. Duncan, R. The dawning era of polymer therapeutics. *Nature Reviews Drug Discovery* 2003, 2 (5), 347-360.
14. Heitz, F.; Morris, M. C.; Divita, G. Twenty years of cell-penetrating peptides: from molecular mechanisms to therapeutics. *British Journal of Pharmacology* 2009, 157 (2), 195-206.
15. Bechinger, B. Peptide-nucleic acid nanostructures for transfection. *Biomol. Concepts.* 2012, 3 (3), 283-293.
16. Varkouhi, A. K.; Scholte, M.; Storm, G.; Haisma, H. J. Endosomal escape pathways for delivery of biologicals. *J. Control. Release* 2011, 151 (3), 220-228.
17. Raagel, H.; Saalik, P.; Pooga, M. Peptide-mediated protein delivery-Which pathways are penetrable? *Biochimica et Biophysica Acta-Biomembranes* 2010, 1798 (12), 2240-2248.
18. Hallbrink, M.; Floren, A.; Elmquist, A.; Pooga, M.; Bartfai, T.; Langel, U. Cargo delivery kinetics of cell-penetrating peptides. *Biochimica et Biophysica Acta-Biomembranes* 2001, 1515 (2), 101-109.
19. Muro, S. Challenges in design and characterization of ligand-targeted drug delivery systems. *J. Control. Release* 2012, 164 (2), 125-137.
20. Maiolo, J. R.; Ottinger, E. A.; Ferrer, M. Specific redistribution of cell-penetrating peptides from endosomes to the cytoplasm and nucleus upon laser illumination. *J. Am. Chem. Soc.* 2004, 126 (47), 15376-15377.
21. Yu, H. J.; Zou, Y. L.; Wang, Y. G.; Huang, X. N.; Huang, G.; Sumer, B. D.; Boothman, D. A.; Gao, J. M. Overcoming Endosomal Barrier by Amphotericin B-Loaded Dual pH-Responsive PDMA-b-PDPA Micelleplexes for siRNA Delivery. *Acs Nano* 2011, 5 (11), 9246-9255.
22. Yao, L.; Daniels, J.; Wijesinghe, D.; Andreev, O. A.; Reshetnyak, Y. K. pHLIP (R)-mediated delivery of PEGylated liposomes to cancer cells. *J. Control. Release* 2013, 167 (3), 228-237.
23. Subbarao, N. K.; Parente, R. A.; Szoka, F. C.; Nadasdi, L.; Pongracz, K. pH-dependent bilayer destabilization by an amphipathic peptide. *Biochemistry* 1987, 26, 2964-2972.
24. Parente, R. A.; Nadasdi, L.; Subbarao, N. K.; Szoka, F. C. Association of a pH-Sensitive Peptide with Membrane Vesicles: Role of Anion Acid Sequence. *Biochemistry* 1990, 29, 8713-8719.
25. Fendos, J.; Barrera, F. N.; Engelman, D. M. Aspartate Embedding Depth Affects pHLIP's Insertion pK(a). *Biochemistry* 2013, 52 (27), 4595-4604.
26. Wiedman, G.; Wimley, W. C.; Hristova, K. Testing the limits of rational design by engineering pH sensitivity into membrane-active peptides. *Biochim. Biophys. Acta* 2015, 1848 (4), 951-957.
27. Parente, R. A.; Nir, S.; Szoka, F. C., Jr. Mechanism of leakage of phospholipid vesicle contents induced by the peptide GALA. *Biochemistry* 1990, 29 (37), 8720-8728.
28. An, M.; Wijesinghe, D.; Andreev, O. A.; Reshetnyak, Y. K.; Engelman, D. M. pH-(low)-insertion-peptide (pHLIP) translocation of membrane impermeable phalloidin toxin inhibits cancer cell proliferation. *Proc. Natl. Acad. Sci. U.S.A* 2010, 107(47), 20246-20250.
29. Nishimura, Y.; Takeda, K.; Ezawa, R.; Ishii, J.; Ogino, C.; Kondo, A. A display of pH-sensitive fusogenic GALA peptide facilitates endosomal escape from a Bio-nanocapsule via an endocytic uptake pathway. *J. Nanobiotechnology* 2014, 12, 11.
30. Endoh, T.; Ohtsuki, T. Cellular siRNA delivery using cell-penetrating peptides modified for endosomal escape. *Advanced Drug Delivery Reviews* 2009, 61 (9), 704-709.

31. Wiedman, G.; Herman, K.; Searson, P.; Wimley, W. C.; Hristova, K. The electrical response of bilayers to the bee venom toxin melittin: Evidence for transient bilayer permeabilization. *Biochim. Biophys. Acta* 2013, 1828 (5), 1357-1364.
32. Krauson, A. J.; He, J.; Wimley, W. C. Gain-of-Function Analogues of the Pore-Forming Peptide Melittin Selected by Orthogonal High-Throughput Screening. *J. Am. Chem. Soc.* 2012, 134 (30), 12732-12741.
33. Wiedman, G.; Fuselier, T.; He, J.; Searson, P. C.; Hristova, K.; Wimley, W. C. Highly Efficient Macromolecule-Sized Poration of Lipid Bilayers by a Synthetically Evolved Peptide. *J. Am. Chem. Soc.* 2014, 136 (12), 4724-4731.
34. Rathinakumar, R.; Walkenhorst, W. F.; Wimley, W. C. Broad-Spectrum Antimicrobial Peptides by Rational Combinatorial Design and High-Throughput Screening: The Importance of Interfacial Activity. *J. Am. Chem. Soc.* 2009, 131 (22), 7609-7617.
35. Krauson, A. J.; He, J.; Wimley, A. W.; Hoffmann, A. R.; Wimley, W. C. Synthetic molecular evolution of pore-forming peptides by iterative combinatorial library screening. *ACS Chem. Biol.* 2013, 8 (4), 823-831.
36. Atherton, E.; Sheppard, R. C. Solid phase peptide synthesis; IRL Press: Oxford, 1989.
37. Wimley, W. C.; Hristova, K.; Ladokhin, A. S.; Silvestro, L.; Axelsen, P. H.; White, S. H. Folding of □-sheet membrane proteins: A hydrophobic hexapeptide model. *J. Mol. Biol.* 1998, 277, 1091-1110.
38. Mayer, L. D.; Hope, M. J.; Cullis, P. R. Vesicles of variable sizes produced by a rapid extrusion procedure. *Biochim. Biophys. Acta* 1986, 858, 161-168.
39. White, S. H.; Wimley, W. C.; Ladokhin, A. S.; Hristova, K. Protein folding in membranes: Determining the energetics of peptide-bilayer interactions. *Methods Enzymol.* 1998, 295, 62-87.
40. Ganz, T.; Selsted, M. E.; Lehrer, R. I. Defensins. *Eur. J. Haematol.* 1990, 44, 1-8.
41. Lehrer, R. I.; Ganz, T.; Selsted, M. E. Defensins—Endogenous Antibiotic Peptides of Animal Cells. *Cell* 1991, 64, 229-230.
42. Brown, K. L.; Hancock, R. E. W. Cationic host defense (antimicrobial) peptides. *Current Opinion in Immunology* 2006, 18 (1), 24-30.
43. Wimley, W. C. Describing the mechanism of antimicrobial peptide action with the interfacial activity model. *ACS Chem. Biol.* 2010, 5 (10), 905-917.
44. Bechinger, B. Structure and function of membrane-lytic peptides. *Critical Reviews in Plant Sciences* 2004, 23 (3), 271-292.
45. Dempsey, C. E. The action of melittin on membranes. *Biochim. Biophys. Acta* 1990, 1031, 143-161.
46. Snider, C.; Jayasinghe, S.; Hristova, K.; White, S. H. MPEx: A tool for exploring membrane proteins. *Protein Sci.* 2009, 18 (12), 2624-2628.
47. Akinc, A.; Thomas, M.; Klibanov, A. M.; Langer, R. Exploring polyethylenimine-mediated DNA transfection and the proton sponge hypothesis. *Journal of Gene Medicine* 2005, 7 (5), 657-663.
48. Erazo-Oliveras, A.; Muthukrishnan, N.; Baker, R.; Wang, T. Y.; Pellois, J. P. Improving the endosomal escape of cell-penetrating peptides and their cargos: strategies and challenges. *Pharmaceuticals. (Basel)* 2012, 5 (11), 1177-1209.
49. van Dyke, R. W. Acidification of lysosomes and endosomes. *Subcellular Biochem.* 1996, 27, 331-360.

The invention claimed is:

1. A polypeptide having at least 85% sequence identity to the sequence of any one of SEQ ID NOs: 1-12.

2. The polypeptide of claim 1, wherein the polypeptide has at least 90%, 95%, 97%, 99%, or 100% sequence identity to any one of SEQ ID NOs: 1-12.

3. The polypeptide of claim 2, wherein the polypeptide has the sequence of SEQ ID NO: 2.

4. The polypeptide of claim 1, wherein the polypeptide forms a pore at a pH of less than about pH 7.0 when the polypeptide is incorporated into a lipid bilayer.

5. The polypeptide of claim 1, wherein the polypeptide:
a) is conjugated to a lipid;

b) further comprises one or more D-amino acids, wherein, optionally, the one or more D-amino acids are independently selected from the group consisting of D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, and D-VAL; and/or c) further comprises one or more derivatized amino acids, wherein, optionally, the one or more derivatized amino acids are selected from the group consisting of N-im-benzylhistidine, 4-hydroxyproline, 5-hydroxylysine, 3-methylhistidine, homoserine, and ornithine; and/or the derivatized amino acid has a chemical moiety selected from the group consisting of amine hydrochloride, p-toluene sulfonyl, carbobenzoxy, t-butyloxycarbonyl, chloroacetyl, formyl, carboxyl, methyl ester, ethyl ester, hydrazide, O-acyl, and O-alkyl.

6. A chimeric protein comprising the polypeptide of claim 1 linked to a second polypeptide.

7. The chimeric protein of claim 6, wherein the second polypeptide enhances stability or immunogenicity of the polypeptide and/or facilitates purification of the polypeptide.

8. A lipid bilayer comprising the polypeptide of claim 1.

9. A lipid vesicle comprising the lipid bilayer of claim 8.

10. The lipid vesicle of claim 9, further comprising a cargo within the lipid vesicle.

11. The lipid vesicle of claim 9, further comprising a targeting molecule or an immunotherapy agent.

12. A composition comprising the polypeptide of claim 1, a chimeric protein comprising the polypeptide linked to a second polypeptide, a lipid bilayer comprising the polypeptide or the chimeric protein, or a lipid vesicle comprising the lipid bilayer and a pharmaceutically acceptable carrier, excipient, or diluent.

13. A method of delivering a cargo to a target cell, the method comprising contacting the target cell with the composition of claim 12, wherein, optionally, the cargo is delivered to the target cell following exposure of the composition to a pH below a predetermined threshold.

14. The polypeptide of claim 5, wherein the lipid is selected from the group consisting of laurate, myristate, palmitate, oleate, cholesterol, and PEG-cholesterol.

15. The chimeric protein of claim 6, wherein the polypeptide is covalently linked to the second polypeptide.

16. The lipid bilayer of claim 8, wherein the polypeptide is linked to a second polypeptide to form a chimeric protein.

17. The lipid bilayer of claim 16, wherein the lipids are phospholipids.

18. The lipid vesicle of claim 10, wherein the cargo is a therapeutic agent.

19. The lipid vesicle of claim 11, wherein the targeting molecule: a) is a receptor, a receptor ligand, an antibody or antigen-binding fragment thereof, or a combination thereof; and/or b) binds to a cancer cell.

20. The composition of claim 12, wherein the composition further comprises a therapeutic agent.

21. The composition of claim 20, wherein the therapeutic agent is an immunotherapy agent.

* * * * *